(12) United States Patent
Nakamura et al.

(10) Patent No.: US 12,370,323 B2
(45) Date of Patent: Jul. 29, 2025

(54) INJECTION DEVICE AND INJECTION UNIT

(71) Applicant: atDose Co., Ltd., Yokohama (JP)

(72) Inventors: Hidenori Nakamura, Yokohama (JP); Satoshi Nakamichi, Yokohama (JP)

(73) Assignee: atDose Co., Ltd., Yokohama (JP)

( * ) Notice: Subject to any disclaimer, the term of this patent is extended or adjusted under 35 U.S.C. 154(b) by 0 days.

(21) Appl. No.: 18/554,715

(22) PCT Filed: May 12, 2023

(86) PCT No.: PCT/JP2023/017870
§ 371 (c)(1),
(2) Date: Oct. 10, 2023

(87) PCT Pub. No.: WO2024/047956
PCT Pub. Date: Mar. 7, 2024

(65) Prior Publication Data
US 2024/0269391 A1 Aug. 15, 2024

(30) Foreign Application Priority Data

Aug. 30, 2022 (JP) ................................. 2022-136543
Sep. 28, 2022 (JP) ................................. 2022-155625

(51) Int. Cl.
*A61M 5/315* (2006.01)
(52) U.S. Cl.
CPC ................................ *A61M 5/3158* (2013.01)
(58) Field of Classification Search
CPC ............ A61M 5/3158; A61M 25/0606; A61M 25/0097; A61M 5/20; A61M 5/31555;
(Continued)

(56) References Cited

U.S. PATENT DOCUMENTS

2005/0187303 A1* 8/2005 Wu .................. A61P 37/08
514/171
2020/0108207 A1* 4/2020 Balan ................ A61B 17/3211
(Continued)

FOREIGN PATENT DOCUMENTS

| CN | 113559361 A | 10/2021 | |
|----|----|----|----|
| DE | 3509865 | * 9/1986 | .......... A61M 5/3156 |
| WO | 2004/028518 A1 | 4/2004 | |

OTHER PUBLICATIONS

Decision to Grant a Patent issued on Dec. 16, 2022, in corresponding Japanese Application No. 2022-155625, 5 pages.

*Primary Examiner* — Lauren P Farrar
*Assistant Examiner* — Kathleen Paige Farrell
(74) *Attorney, Agent, or Firm* — Maier & Maier, PLLC

(57) ABSTRACT

An injection device includes a syringe including a body having an opening, a conversion portion, a button, and a slider. The button includes a pair of leg portions disposed so as to straddle the conversion portion and having front slopes inclined with respect to a tip direction by a set angle. The conversion portion includes a pair of engaging portions connected to a rear end portion of a gasket and having rear slopes that slidingly contact the front slopes of the leg portions. The slider moves the conversion portion and button in the tip direction. The conversion portion moves in the tip direction along with the gasket in accordance with an operation of pushing down the button toward the inside of the body. An injection unit includes the injection device and one or more adjustment members configured to adjust the frontmost position of the button in the opening.

2 Claims, 31 Drawing Sheets

(58) Field of Classification Search
CPC ............ A61M 5/24; A61M 2005/2073; A61M 25/0625; A61M 5/31501; A61M 5/31563; A61M 5/3271; A61M 2005/2026
See application file for complete search history.

(56) References Cited

U.S. PATENT DOCUMENTS

2021/0260338 A1\* 8/2021 Scherich ............ A61M 25/0631
2023/0390532 A1\* 12/2023 Mr .................... A61M 25/0606

\* cited by examiner

INJECTION DEVICE AND INJECTION UNIT

FIELD

The present invention relates to an injection device and injection unit used to inject a chemical solution into a body.

BACKGROUND

Injection devices have been known as tools for injecting a chemical solution into a body (see Patent Literatures 1 and 2). Such an injection device is configured to eject a chemical solution charged between a syringe and a gasket from a needle mounted on the tip of the syringe in accordance with an operation of pushing in a plunger disposed on the rear end of the gasket.

PATENT LITERATURE

[Patent Literature 1] Japanese Unexamined Patent Application Publication No. 2010-167279
[Patent Literature 2] Japanese Unexamined Patent Application Publication No. 2012-249716

SUMMARY

However, in the case of the conventional injection device, a user has to remove air by operating the plunger, then to stick the needle into a blood vessel, muscle, or the like while holding the tip of the syringe, and then to inject the chemical solution while holding the plunger. As seen above, in the case of the conventional injection device, the user has to switch the injection device area to be held between the syringe tip and the plunger in the course from the removal of air to the injection of the chemical solution, and the series of operations related to injection are troublesome. Moreover, when holding the plunger after sticking the needle, the needle tip may be shaken. This may damage a cell or tissue of skin or cause pain to an injection subject such as a patient.

The present invention has been made to solve the above problems, and an object thereof is to provide an injection device and injection unit that do not require frequent switching of the injection device area to be held and reduce the load on the injection subject.

Solution to Problem

An injection device according to one aspect of the present invention includes a syringe including a tubular body, the body having, in a peripheral wall, an opening having a rectangular shape in a plan view, a conversion portion connected to a rear end portion of a gasket disposed on a tip side of the body, the conversion portion being contained in the body, a button disposed on a side near the opening of the conversion portion and supported by the conversion portion with side portions of the button sandwiched between both side walls of the opening, and a slider disposed in the opening in the peripheral wall of the body and configured to move the conversion portion and the button in a tip direction that is a direction in which the gasket moves toward a tip of the body. The button has a cross-sectional U-shape on a plane perpendicular to the tip direction and includes a pair of leg portions disposed so as to straddle the conversion portion and having front slopes inclined with respect to the tip direction by a set angle. The conversion portion includes a pair of engaging portions formed so as to correspond to the pair of leg portions and having rear slopes that slidingly contact the front slopes and is configured to move in the tip direction in accordance with an operation of pushing down the button toward inside of the body.

An injection unit includes the above injection device and one or more adjustment members configured to adjust the frontmost position of the button in the opening. The one or more adjustment members include a spacer having a preset width and disposed between the side walls of the opening.

Advantageous Effects of the Invention

The present invention includes the conversion portion contained in the body, the button supported by the conversion portion with the side portions thereof sandwiched between the side walls of the opening, and the slider configured to move the conversion portion and button in the tip direction. The button includes the pair of leg portions having the front slopes, and the conversion portion includes the pair of engaging portions having the rear slopes. Thus, a user is able to remove air by operating the slider located on the peripheral wall of the body so that the conversion portion to which the gasket is connected moves in the tip direction and to inject a chemical solution to a human, animal, or the like by operating the button located on the peripheral wall of the body so that the conversion portion further moves in the tip direction. This eliminates frequent switching of the injection device area to be held from the series of operations related to injection and reduces the load on the injection subject.

DETAILED DESCRIPTION

First Embodiment

Figure 1:
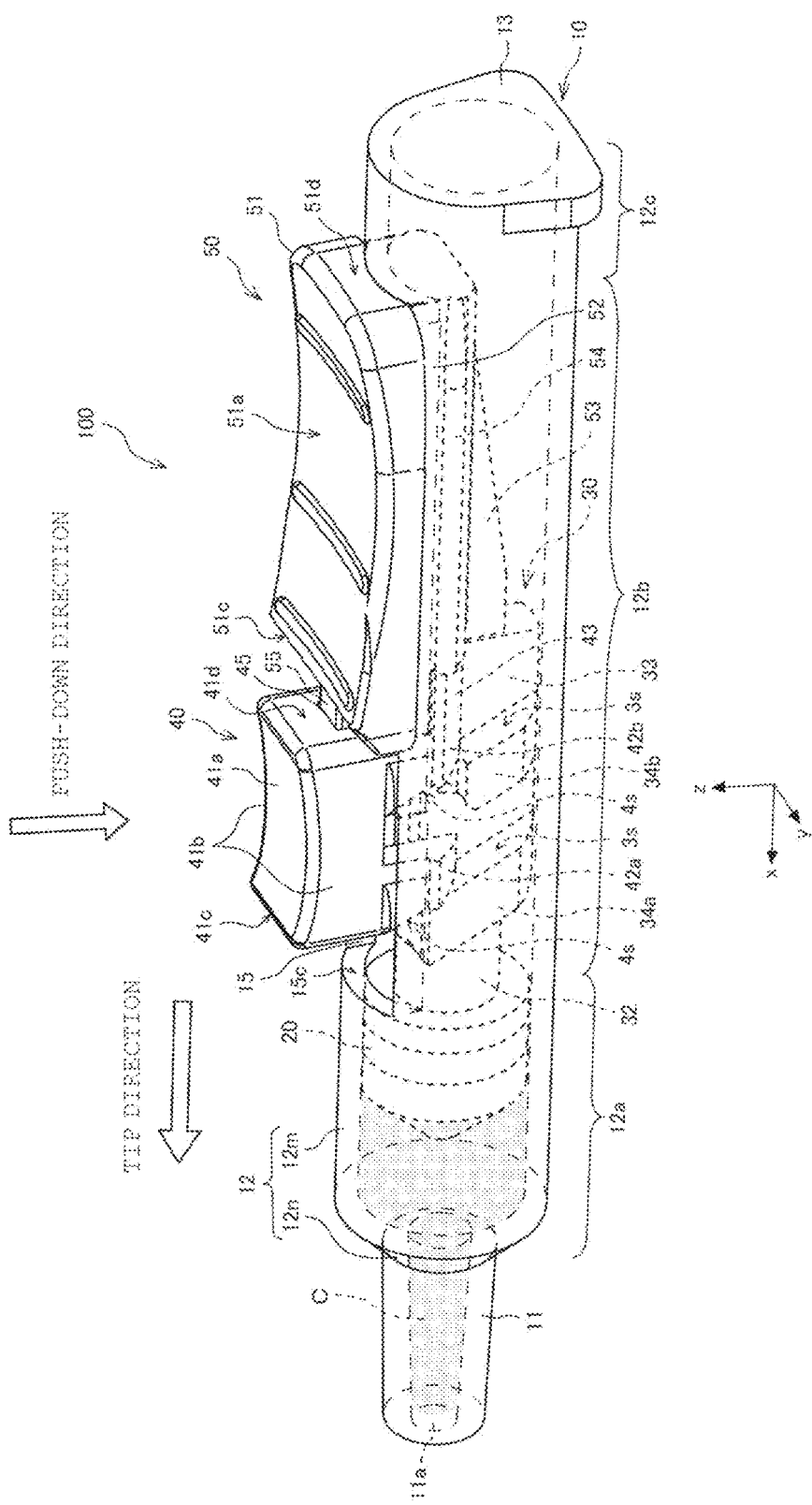
FIG. 1 is a perspective view showing an example configuration of an injection device according to a first embodiment of the present invention.

Referring to FIGS. 1 to 12, an example configuration of an injection device 100 according to a first embodiment will be described. For convenience, an x-axis direction, a y-axis direction, and a z-axis direction in the drawings are referred to as a front-rear direction, a left-right direction, and an up-down direction, respectively. In the following description, these directions may be used to describe the orientations of the members or the positional relationships therebetween. To avoid complication, some of reference signs or the like are omitted in the drawings as appropriate.

Figure 2:
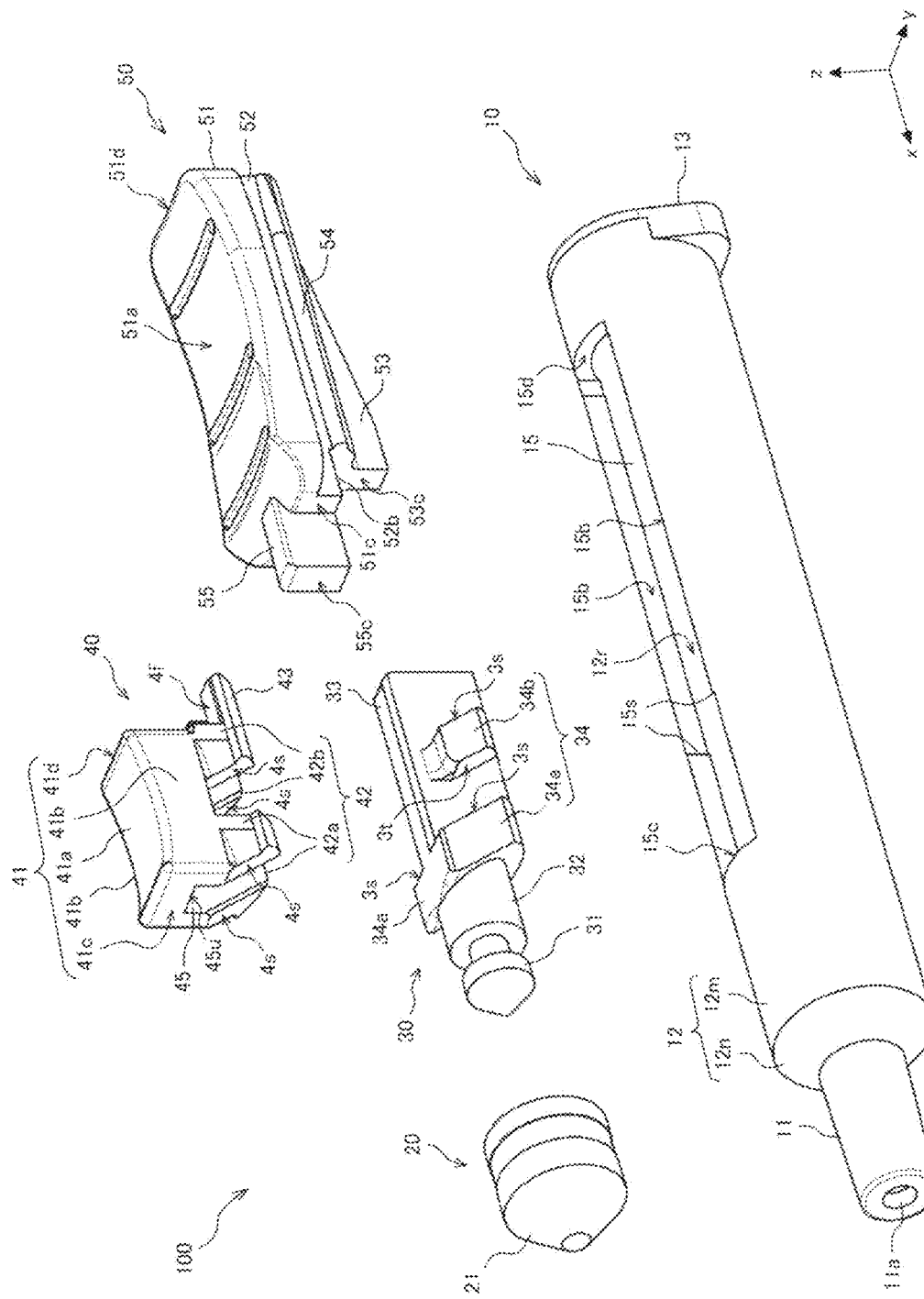
FIG. 2 is an exploded perspective view illustrating the individual members of the injection device in FIG. 1.
Figure 3:
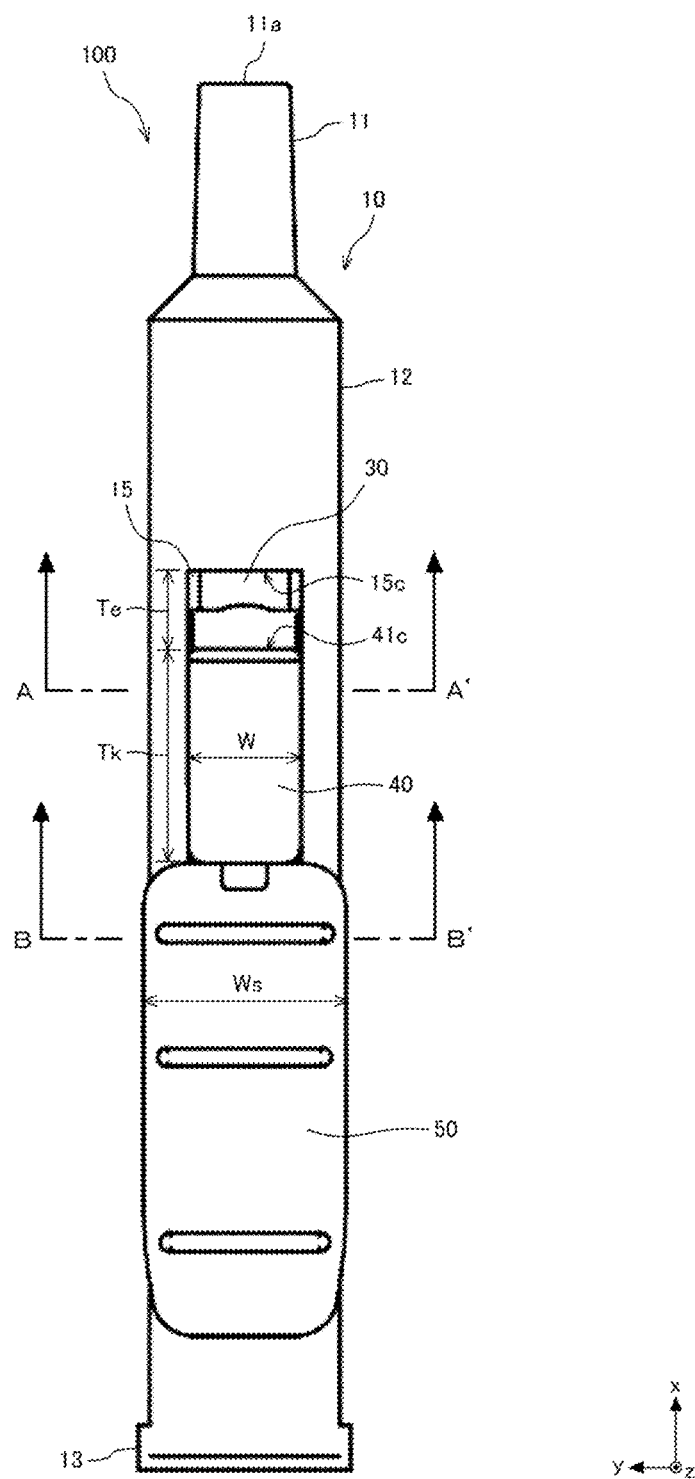
FIG. 3 is a plan view of the injection device in FIG. 1 seen from above.

First, referring to FIGS. 1 to 3, an example overall configuration of the injection device 100 according to the first embodiment will be described. As shown in FIGS. 1 to 3, the injection device 100 includes a syringe 10, a gasket 20, a conversion portion 30, a button 40, and a slider 50.

Suitable materials of the syringe 10 include polypropylene (PP), cycloolefin polymer (COP), polystyrene (PS), polycarbonate (PC), and the like, which have transparency. In FIG. 1, the gasket 20, conversion portion 30, button 40, and slider 50 seen behind the syringe 10 are shown by broken lines, and the inner wall of the syringe 10, and the like are also shown by broken lines.

The syringe 10 includes a cylinder tip portion 11, a body 12, and a lid portion 13. The body 12 is formed in a cylindrical shape, and the cylinder tip portion 11 is connected to the tip thereof. More specifically, the body 12 includes a cylindrical peripheral wall 12m, as well as includes a tip portion 12n for connecting the peripheral wall 12m and cylinder tip portion 11. The tip portion 12n illustrated in FIG. 1 and the like is tapered from the peripheral wall 12m toward the cylinder tip portion 11. The peripheral wall 12m of the body 12 is provided with an opening 15 having a rectangular shape in a plan view.

The body 12 can be divided into a chemical solution storage portion 12a, a mechanism incorporation portion 12b, and an auxiliary portion 12c in terms of functionality. The chemical solution storage portion 12a is a portion into which the gasket 20 is to be fitted and a chemical solution C is to be charged. The mechanism incorporation portion 12b is a portion provided with the opening 15 and incorporates an push-out mechanism for pushing out the gasket 20 in two stages. The push-out mechanism is a mechanism obtained by combining the conversion portion 30, button 40 and slider 50. The auxiliary portion 12c has a length set on the basis of the operability of the injection device 100, or the like and has the lid portion 13 mounted on the rear end portion thereof.

The cylinder tip portion 11 is a cylindrical member having a smaller inner and outer diameters than those of the body 12. The cylinder tip portion 11 is a portion that has an ejection hole 11a on the tip thereof and into which an injection needle (not shown) is to be inserted. The lid portion 13 is a portion for reinforcing the rear end portion of the body 12. The lid portion 13 illustrated in FIG. 1 and the like has a perimeter consisting of a flat portion and a curved portion, and the flat portion is disposed on the side opposite to that on which the opening 15 disposed. By using the lid portion 13 thus shaped, the user is able to stably place the injection device 100 with the button 40 oriented upward and thus to prevent the injection device 100 from rolling.

The gasket 20 is a portion disposed near the tip of the body 12 and is made of an elastic material such as rubber. The gasket 20 is formed in a cylindrical shape so as to closely contact the inner wall 12r of the body 12. The front end portion 21 of the gasket 20 is formed so as to match the shape of the inner surface of the tip of the chemical solution storage portion 12a. The front end portion 21 of the gasket 20 according to the first embodiment is tapered. The rear end portion of the gasket 20 is provided with a connection hole (not shown) for connecting with the conversion portion 30.

The button 40 is disposed on the opening 15 side of the conversion portion 30 and supported by the conversion portion 30 with the sides thereof sandwiched between both side walls 15b (left and right side walls 15b) of the opening 15. The button 40 has a cross-sectional U-(concave) shape on a plane perpendicular to a tip direction. The tip direction refers to the direction in which the gasket 20 is oriented toward the tip of the body 12 and corresponds to the positive x-axis direction, that is, the forward direction in the drawings.

The button 40 includes a face wall 41a to be pushed by a finger or the like and a pair of side walls 41b extending approximately perpendicularly to the face wall 41a from both side end portions of the face wall 41a. FIG. 1 shows the initial state, which is a state in which the slider 50 is in contact with the rear wall 15d of the opening 15 and the button 40 is in contact with the push end surface 51c of the slider 50. In the initial state, the button 40 is disposed such that the front end surface 41c thereof is opposed to the front wall 15c of the opening 15 and the rear end surface 41d thereof is in contact with the push end surface 51c. As shown in FIG. 2, a portion including the face wall 41a and the pair of side walls 41b and having the front end surface 41c and rear end surface 41d of the button 40 is referred to as a button body 41.

The length Te (see FIG. 3) of the gap between the front end surface 41c of the button 40 and the front wall 15c of the opening 15 in the initial state is set to a length that allows the user to remove air accumulated in the injection needle mounted on the tip of the cylinder tip portion 11 and the chemical solution storage portion 12a through the tip of the injection needle. That is, the length Te is set in order to remove air through the tip of the injection needle.

The button 40 has a pinching groove 45 formed along the tip direction from the rear end surface 41d. The pinching groove 45 according to the first embodiment is formed so as to range from the rear end surface 41d to the front end surface 41c of the button 40. When the button 40 is pushed down, the pinching groove 45 pinches the core portion 33 of the conversion portion 30. The button 40 includes a pair of leg portions 42 disposed so as to straddle the conversion portion 30 and each having front slopes 4s inclined with respect to the tip direction by a set angle θ.

The pair of leg portions 42 shown in the drawings each include a first leg portion 42a disposed on the gasket 20 side and a second leg portion 42b disposed on the slider 50 side. That is, the button 40 includes the pair of first legs 42a and the pair of second legs 42b. Hereafter, the first leg portion 42a and second leg portion 42b may be collectively referred to as the leg portion 42 without distinguishing them from each other. The first leg portion 42a and second leg portion 42b have, on the front side thereof, the front slopes 4s that slidingly contact the rear slopes 3s of the conversion portion 30. The button 40 also includes a pair of come-out prevention portions 43 that extend rearward from lower portions of the second leg portion 42b and are to be engaged with the bottom portion 52b of a pinching portion 52. The bottom portion 52b is a front-side portion of the bottom (lower surface) of the pinching portion 52 exposed from the auxiliary portion 53. The button 40 is disposed such that flat surfaces 4f of upper portions of the come-out prevention portions 43 are opposed to the bottom portion 52b of the pinching portion 52. Thus, the come-out prevention portions 43 are caught on the bottom portion 52b and prevent the button 40 from falling down.

The conversion portion 30 is connected to the rear end portion of the gasket 20 and contained in the body 12. The conversion portion 30 includes a fitting portion 31 to be fitted into the connection hole of the gasket 20, a neck portion 32 connected to the fitting portion 31, the plate-shaped core portion 33 connected to the neck portion 32, and a pair of engaging portions 34 disposed on both side surfaces of the core portion 33. The pair of engaging portions 34 are formed so as to correspond to the pair of leg portions 42 and have rear slopes 3s that slidingly contact the front slopes 4s. That is, the inclination of the rear slopes 3s is equal to the inclination of the front slopes 4s. The conversion portion 30 is configured to move in the tip direction in accordance with an operation of pushing down the button 40 toward the inside of the body 12. The direction in which the button 40 is pushed down toward the inside of the body 12 is a direction perpendicular to the tip direction and is hereafter also referred to as a "push-down direction." The push-down direction corresponds to the negative z-axis direction in the drawings.

The engaging portions 34 shown in the drawings each include a first engaging portion 34a disposed on the gasket 20 side and a second engaging portion 34b disposed on the slider 50 side. The first engaging portion 34a corresponds to the first leg portion 42a and has the rear slope 3s that slidingly contacts the front slope 4s of the first leg portion 42a. The second engaging portion 34b corresponds to the second leg portion 42b and has the rear slope 3s that slidingly contacts the front slope 4s of the second leg portion 42b.

While the drawings show an example in which the second engaging portions 34b of the conversion portion 30 have front auxiliary slopes 3t inclined with respect to the tip direction by the set angle θ, this example corresponds to a modification B (to be discussed later). That is, the second engaging portions 34b need not have the front auxiliary slopes 3t.

The slider 50 is disposed behind the conversion portion 30 and button 40. The slider 50 is a portion for moving the conversion portion 30 and button unit 40 in the tip direction. The slider 50 includes an operation portion 51, the pinching portion 52, the auxiliary portion 53, and a safety protrusion 55. The operation portion 51 is disposed outside the body 12, and the width Ws thereof is wider than the width ($W_2$) of the opening 15. The pinching portion 52 is connected to the surface opposite to the operation surface 51a of the operation portion 51 and is disposed so as to be sandwiched between the side walls 15b of the opening 15. The width of the pinching portion 52 is equal to or slightly smaller than the width ($W_2$) of the opening 15.

The auxiliary portion 53 is connected to the surface opposite to the surface of the pinching portion 52 connected to the operation portion 51 and is disposed inside the body 12. The auxiliary portion 53 is formed such that a step is formed between the auxiliary portion 53 and the pinching portion 52 on the button 40 side. The bottom portion 52b to be engaged with the come-out prevention portions 43 is a front-lower portion of the pinching portion 52 that is void of the auxiliary portion 53. The auxiliary portion 53 includes a pair of protruding portions 54 formed along the tip direction so as to contact the inner wall 12r of the body 12. The pair of protruding portions 54 prevents the slider 50 from falling down and assists the slider 50 in stably sliding. The auxiliary portion 53 has an auxiliary end surface 53c disposed so as to be opposed to the rear end surface of the core portion 33 and the rear end surfaces of the come-out prevention portions 43. That is, the slider 50 is able to stably push out the conversion portion 30 and button 40 using the push end surface 51c and auxiliary end surface 53c.

The safety protrusion 55 is disposed on the button 40 side of the operation portion 51 and is formed so as to be insertable into the pinching groove 45 of the button 40. In a stretched state, the tip end surface 55c of the safety protrusion 55 is flush with the rear end surface 41d. The stretched state is a state in which the button 40 is disposed in the frontmost position in the opening 15 and the slider 50 is disposed in the rearmost position in the opening 15. In the first embodiment, the frontmost position of the button unit 40 in the opening 15 is the position in which the button 40 contacts the front wall 15c, and the rearmost position of the slider 50 in the opening 15 is the position in which the slider 50 contacts the rear wall 15d. Thus, when the user pushes down the button 40, the button 40 moves in the push-down direction with the rear end surface 41d contacting the tip end surface 55c. Since, in the stretched state, the rear end surface 51d of the slider 50 is in contact with the rear wall 15d of the opening 15, movement in the front-rear direction of the button 40 is suppressed by the safety protrusion 55. This prevents rearward movement of the button 40 and the conversion portion 30 engaged therewith. Thus, the movement in the push-down direction of the button 40 is converted into movement in the tip direction of the conversion portion 30 as it is.

The safety protrusion 55 illustrated in the drawings is disposed so as to range from the operation portion 51 to the pinching portion 52. That is, the height in the up-down direction of the safety protrusion 55 is the sum of the height of a portion thereof connected to the operation portion 51 and the height of a portion thereof connected to the pinching portion 52. Thus, until the push-down of the button 40 is complete, the safety protrusion 55 is able to ensure a predetermined contact range between the safety protrusion 55 and the button 40 and to guide the button 40 downward in a stable state. Note that the safety protrusion 55 may be connected only to the operation portion 51.

The push-out mechanism is assembled to the syringe 10, for example, in the following order.

(1) The gasket 20 is fitted into the conversion portion 30.

(2) The conversion portion 30 having the gasket 20 fitted thereinto is inserted into the hole of the rear end of the syringe 10 with the gasket 20 oriented in the tip direction.

(3) The button 40 is fitted into the opening 15 so as to correspond to the conversion portion 30.

(4) The slider 50 is fitted into a rear portion of the button 40 through the opening 15.

(5) Individual members are disposed behind the syringe 10 using thin pins or the like.

The chemical solution C is charged into the chemical solution storage portion 12a, for example, by inserting a thin pipe such as a cannula into the tip of the cylinder tip portion 11. The conversion portion 30, button 40, and slider 50 are integrally made of a resin or the like.

Figure 4:
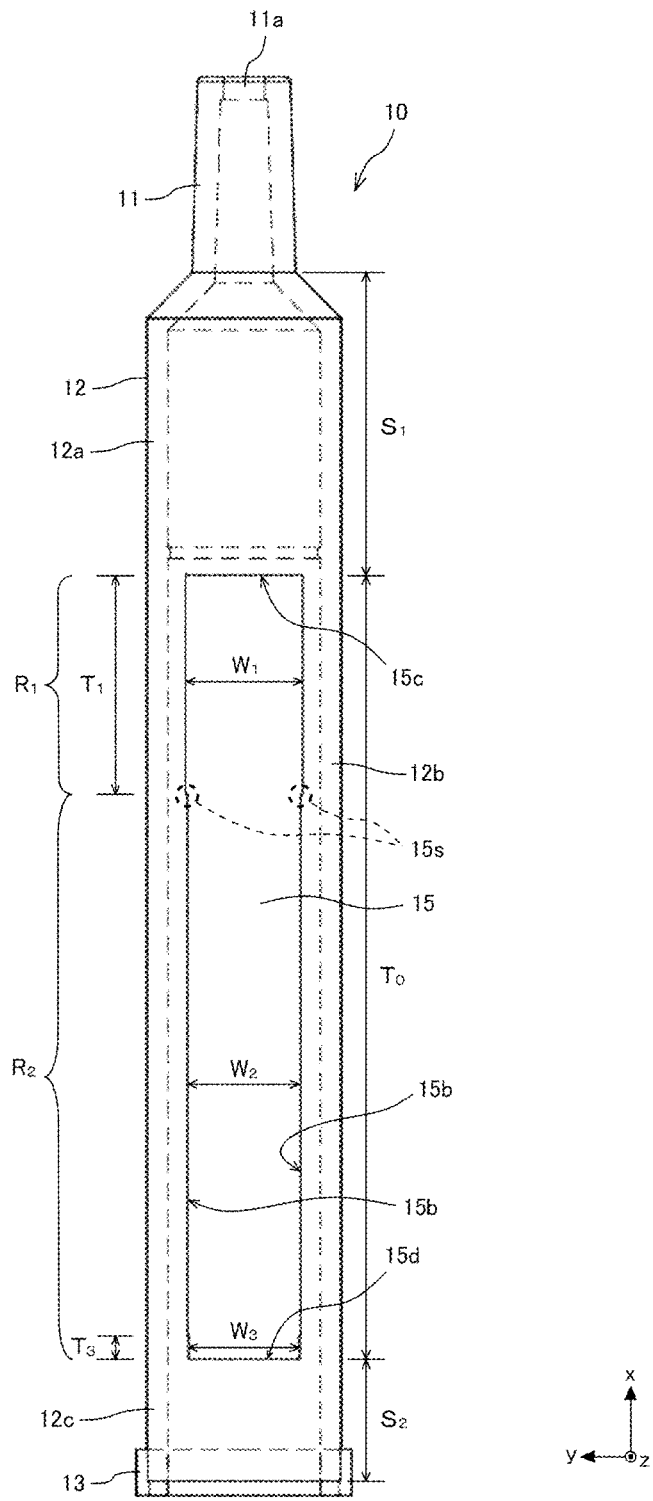
FIG. 4 is a plan view of a syringe in FIG. 1 seen from above.

Next, referring to FIG. 4, a specific example configuration of the syringe 10 will be described below. As shown in FIG. 4, the length of the chemical solution storage portion 12a is represented by $S_1$, the length of the mechanism incorporation portion 12b, that is, the length of the opening 15 is represented by $T_0$, and the length of the auxiliary portion 12c is represented by $S_2$. The length $S_1$ is set on the basis of the size of the gasket 20, the preset dose of the chemical solution C, or the like. The front wall 15c may be formed such that the position thereof in the tip direction is substantially variable. That is, the syringe 10 may be configured such that the ratio between the length $S_1$ and the length $T_0$ can be adjusted. Thus, the dose of the chemical solution C can be adjusted, for example, by matching the amount of movement L corresponding to a stroke H with that when the length $S_1$ is maximized. The length $S_2$ is set in terms of the strength of the syringe 10, the ease of holding, or the like. The length $T_0$ is set such that the tip end surface 55c of the safety protrusion 55 becomes flush with the rear end surface 41d of the button 40 in the stretched state.

A portion of the opening 15 extending in the tip direction from the position of the rear end surface 41d of the button 40 disposed in the frontmost position in the opening 15 is wider than the other portion. In the first embodiment, the frontmost position of the button unit 40 in the opening 15 is the position in which the button 40 contacts the front wall 15c. That is, the side walls 15b of the opening 15 are provided with steps 15s in positions of the rear end surface 41d of the button 40 in contact with the front wall 15c. The button 40 in contact with the front wall 15c is prevented from moving rearward by the step 15s, which are narrower rearward. Thus, when the user contacts the button 40 with the front wall 15c and then moves the slider 50 rearward, a situation in which the button 40 moves rearward in conjunction with the movement of the slider 50 is avoided.

The length $T_1$ of a region $R_1$ from the front wall 15c to the step 15s is set on the basis of the length Tk of the button 40. In the first embodiment, the length $T_1$ is set so as to be equal to or slightly longer than the length Tk. The width $W_1$ of the region $R_1$ is set such that the resistance during operation is minimized, in consideration of the smoothness, stability, and the like of the push-down operation of the button 40. The width of a region $R_2$ from the step 15s to the rear wall 15d is narrower than the width $W_1$ as a whole. In the first embodiment, with respect to the width of the region $R_2$, the width $W_3$ of a portion inside the rear wall 15d corresponding to a length $T_3$ is narrower than the width $W_2$ of the other portion. Narrowing the width near the rear wall 15d in this manner is intended to fix the slider 50 in contact with the rear wall 15d. For this reason, the length $T_3$ is set so as to correspond to the rear end portion of the slider 50 and is much shorter than the length $T_0$, as shown in FIG. 4. It is preferable to properly adjust the width $W_2$ to the extent that the slidability of the button 40 and slider 50 is not impaired.

Next, referring to FIGS. 5 and 6, a specific configuration of the button 40 will be described. The pair of leg portions 42 each include base portions 4a extending from one of the side walls 41b. In a state in which the button 40 has yet to be pushed down, the base portions 4a are disposed so as to be opposed to the side wall 15b of the opening 15. The base portions 4a according to the first embodiment have inwardly recessed depressions 4k in tip direction-side positions thereof adjacent to the side wall 15b of the opening 15. In an example in FIG. 5, the first leg portions 42a and second leg portions 42b have the depressions 4k. For this reason, the base portions 4a sandwiched between the side walls 15b of the opening 15 are more likely to move in the tip direction and less likely to move rearward. Thus, when the user contacts the button 40 with the front wall 15c and then moves the slider 50 rearward, movement of the button 40 in conjunction with the movement of the slider 50 is suppressed. By disposing the steps 15s in the opening 15 and forming the depressions 4k in the pair of leg portions 42, rearward movement of the button 40 is more accurately prevented.

Figure 5:
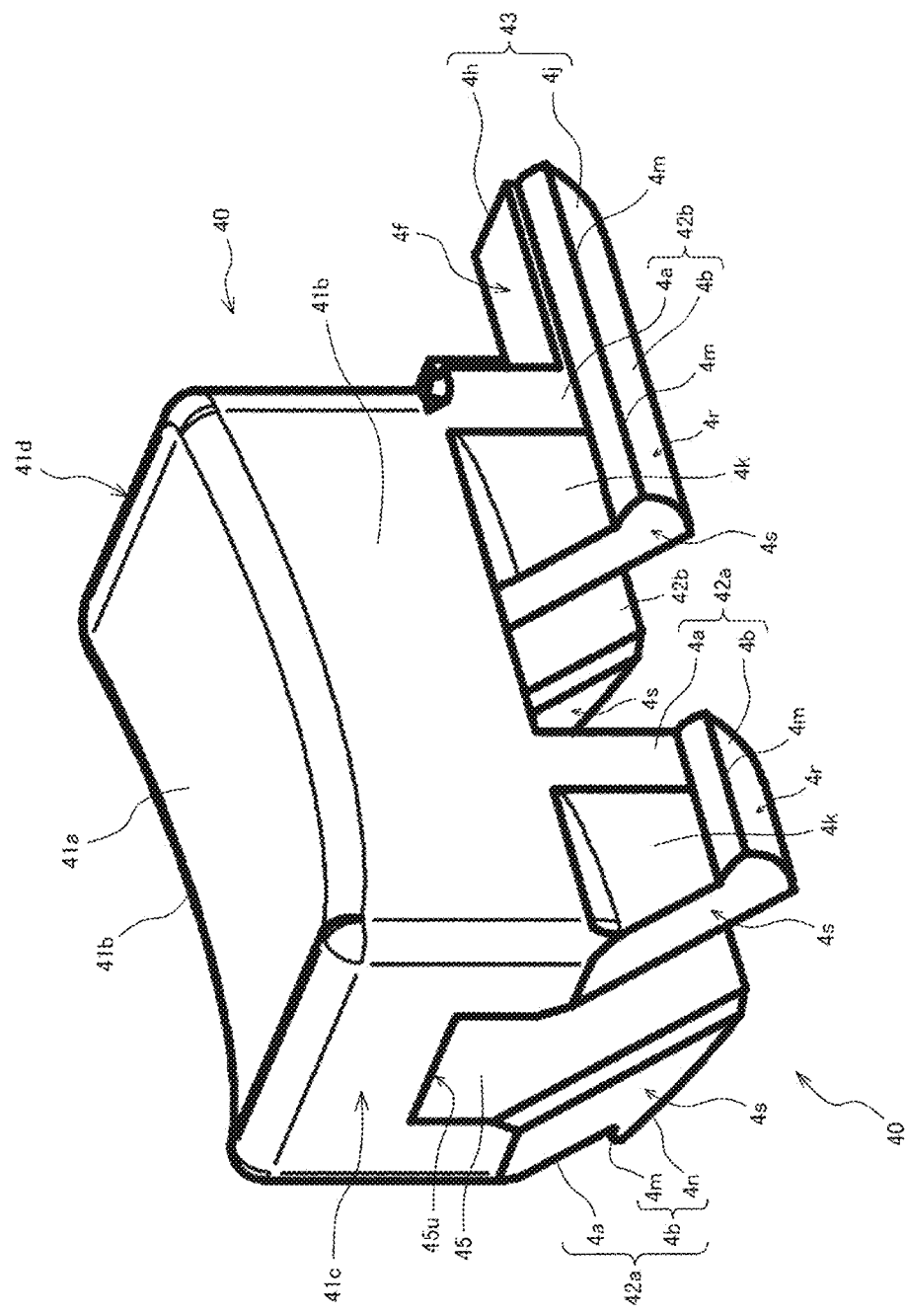
FIG. 5 is an enlarged view showing a button in FIG. 2.
Figure 6:
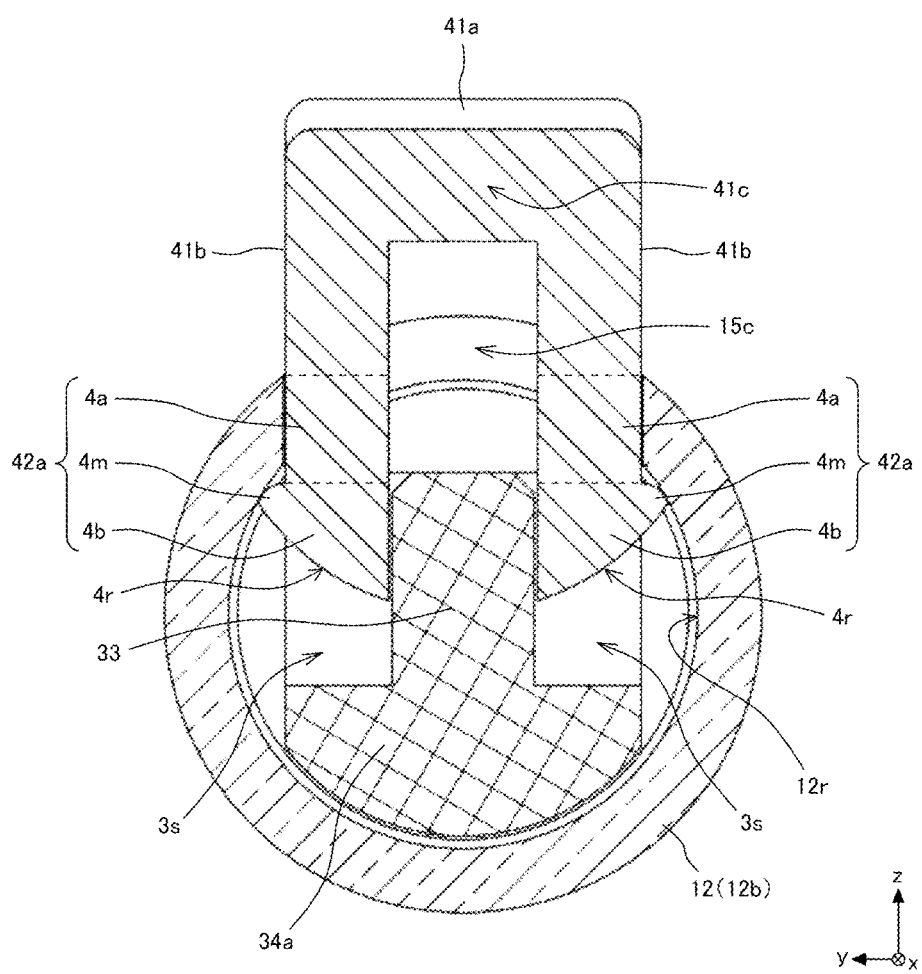
FIG. 6 is a schematic sectional view taken along line A-A' in FIG. 3.

As illustrated in FIG. 5, the first leg portions 42a and second leg portions 42b each include the base portion 4a extending from the side wall 41b and a fitting portion 4b extending from the base portion 4a. The fitting portion 4b includes a protruding portion 4m formed along the tip direction so as to contact the inner wall 12r of the body 12. As shown in FIG. 6, the protruding portions 4m are disposed on the pair of leg portions 42 and prevent the button 40 from falling down and assist the button 40 in stably sliding.

The opposed surfaces 4r of the fitting portions 4b are formed in a curved shape along the inner wall 12r. The opposed surfaces 4r of the fitting portions 4b are portions disposed so as to be opposed to the inner wall 12r of the body 12. Thus, as is understood from FIG. 6, in a state in which the button 40 has yet to be pushed, the range in which the pair of leg portions 42 and the core portion 33 are opposed to each other is increased. This increases the stability of the button 40 that is being pushed down. Also, the opposed surfaces 4r are curved to a degree similar to that of the inner wall 12r of the body 12. Thus, when the button 40 is pushed down, the lower end portions of the fitting portions 4b are brought close to the inner wall 12r of the body 12 or its vicinity. Thus, the stroke H, which is the distance by which the button 40 can be pushed down, is maximized.

The come-out prevention portions 43 illustrated in FIG. 5 include plate-shaped flat portions 4h and fitting portions 4j having a shape similar to that of the fitting portions 4b. That is, the protruding portions 4m are disposed so as to extend from the second leg portions 42b to the come-out prevention portions 43, and the opposed surfaces 4r are formed in a curved shape along the inner wall 12r so as to extend from the second leg portions 42b to the come-out prevention portions 43.

Figure 7:
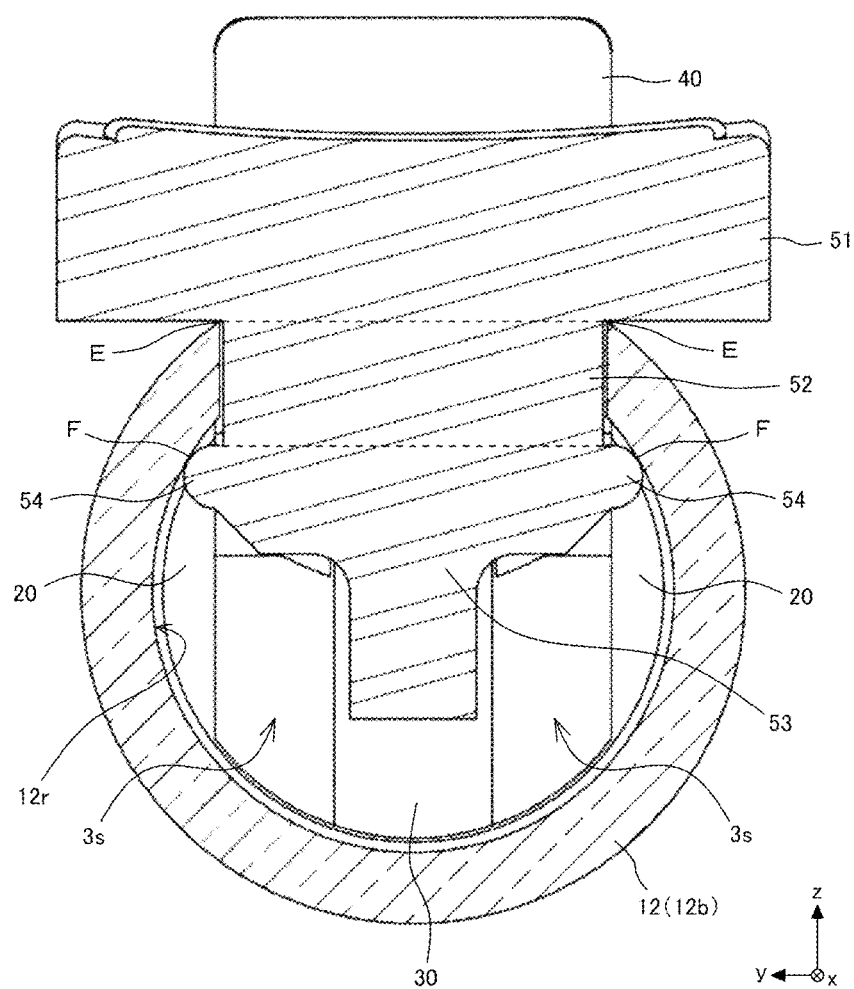
FIG. 7 is a schematic sectional view taken along line B-B' in FIG. 3.

Next, referring to FIG. 7, the positional relationship between the slider 50 and body 12 will be described. In FIG. 7, the boundaries between the members are shown by broken lines for convenience. As shown in FIG. 7, left and right corners E located on the boundary between the operation portion 51 and pinching portion 52 extend linearly along the front-rear direction and are supported by the upper end of the opening 15. The width of the slider 50 in the positions of the pair of protruding portions 54 is wider than the width ($W_2$) of the opening 15, and the contact ends F of the protruding portions 54 can contact the inner wall 12r. The contact ends F of the pair of protruding portions 54 extend linearly along the front-rear direction. That is, the slider 50 is shaped such that the pinching portion 52 between the operation portion 51 and protruding portions 54 is relatively recessed in a cross-sectional view. The positions of the side walls 15b of the opening 15 of the syringe 10 are constrained by the corners E and contact ends F of the slider 50 (two-line constraint). Thus, the opening 15 serves as a rail for causing the slider 50 to stably slide.

Next, referring to FIGS. 8 to 11, a series of operations related to injection using the injection device 100 will be described. To clearly show the operating state of the push-out mechanism, FIGS. 8 to 11 illustrate the syringe 10 whose half is cut off. In these drawings, the portion into which the chemical solution C is charged is dotted so that the movement of the chemical solution C is clarified.

Figure 8:
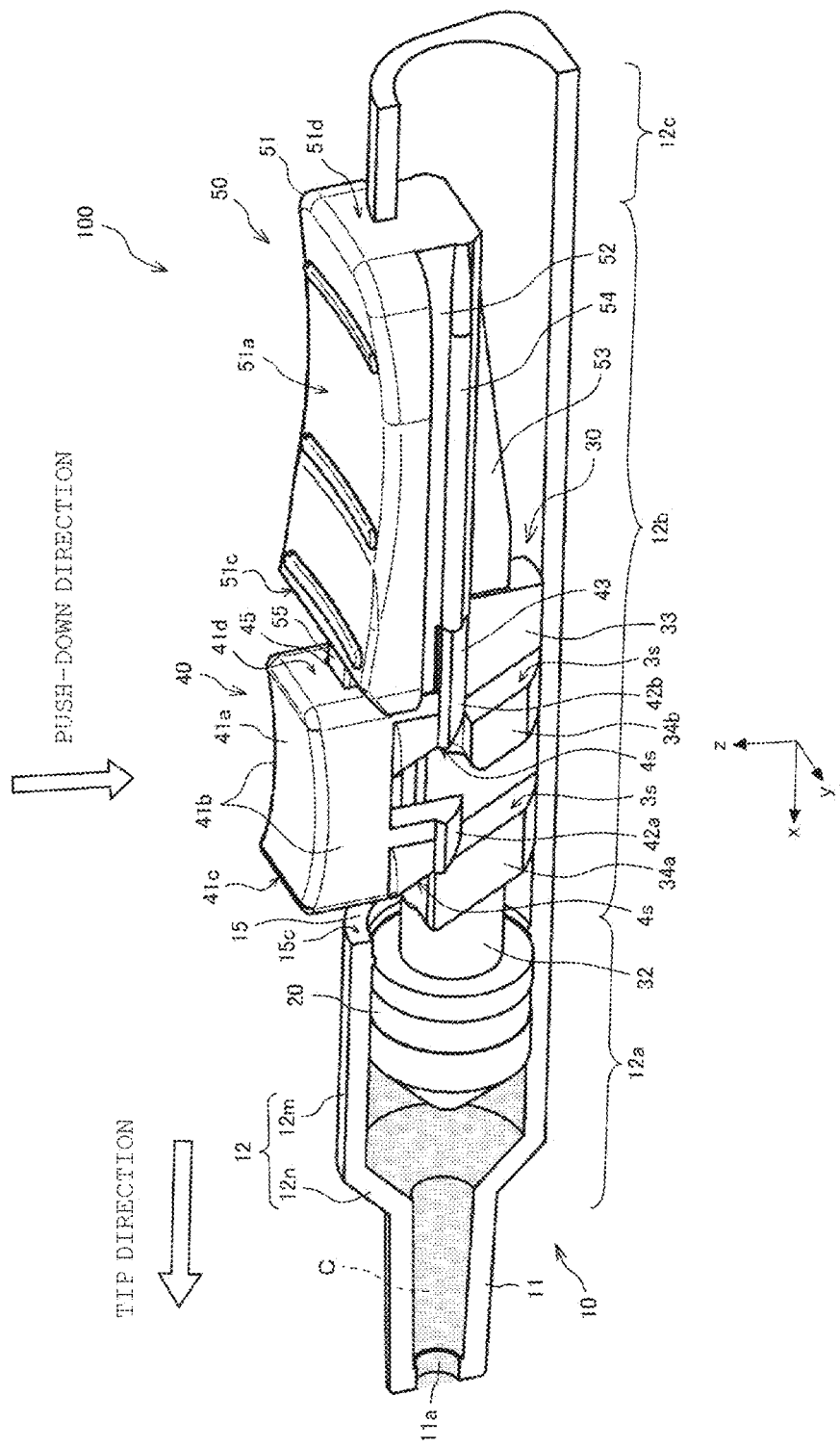
FIG. 8 is a drawing illustrating the initial state of the injection device in FIG. 1.
Figure 9:
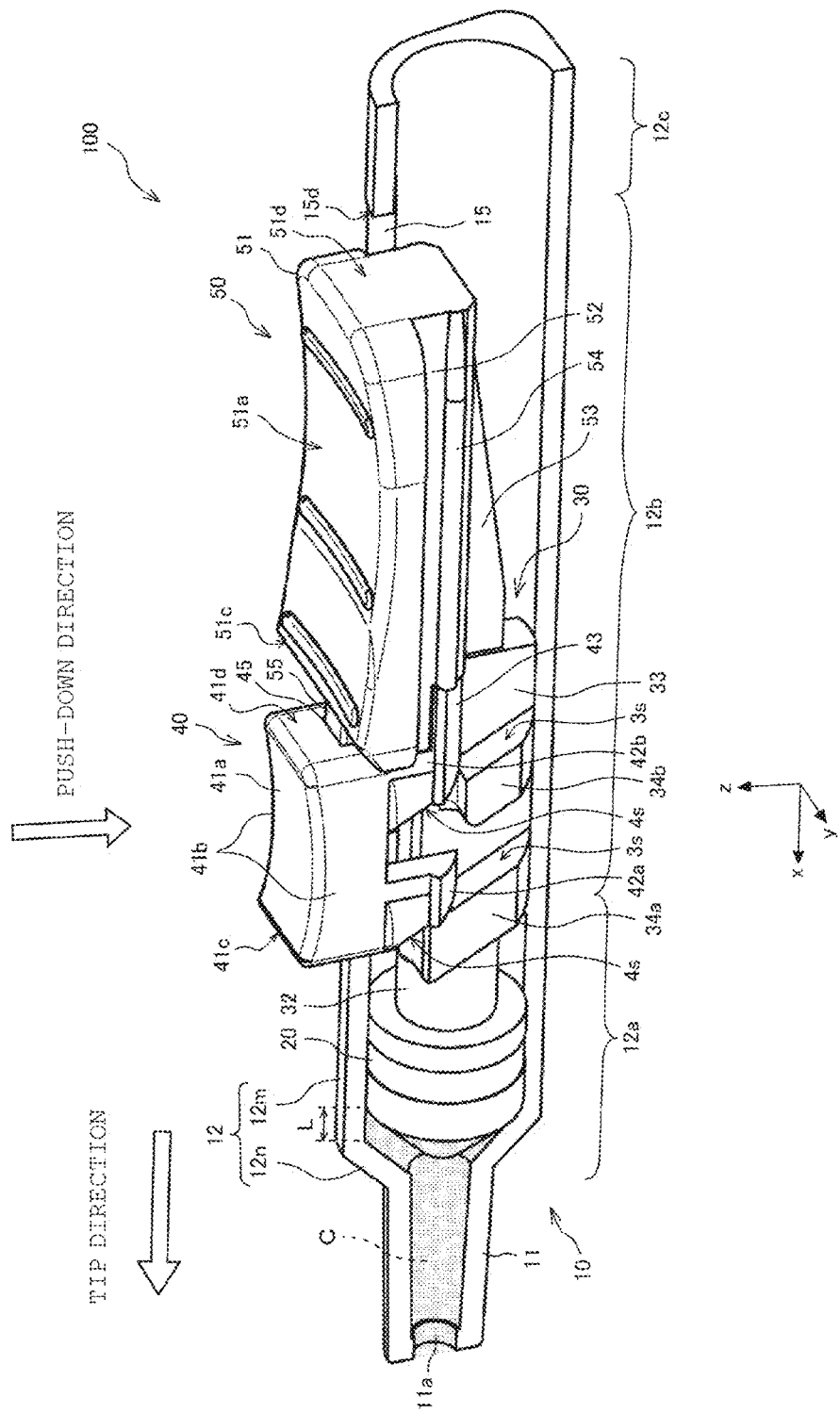
FIG. 9 is a drawing illustrating the push-out state of the injection device in FIG. 1.
Figure 10:
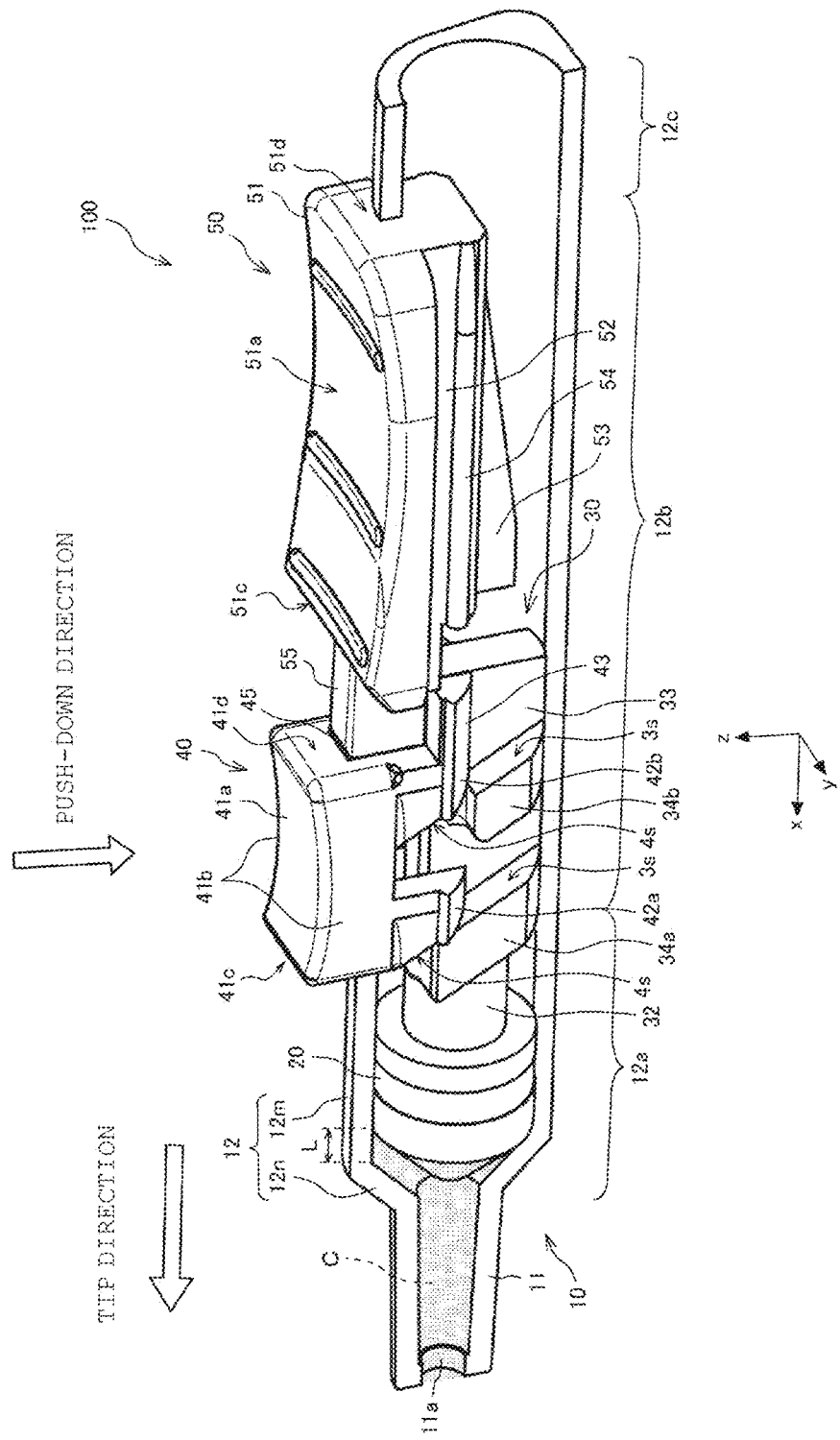
FIG. 10 is a drawing illustrating the stretched state of the injection device in FIG. 1.
Figure 11:
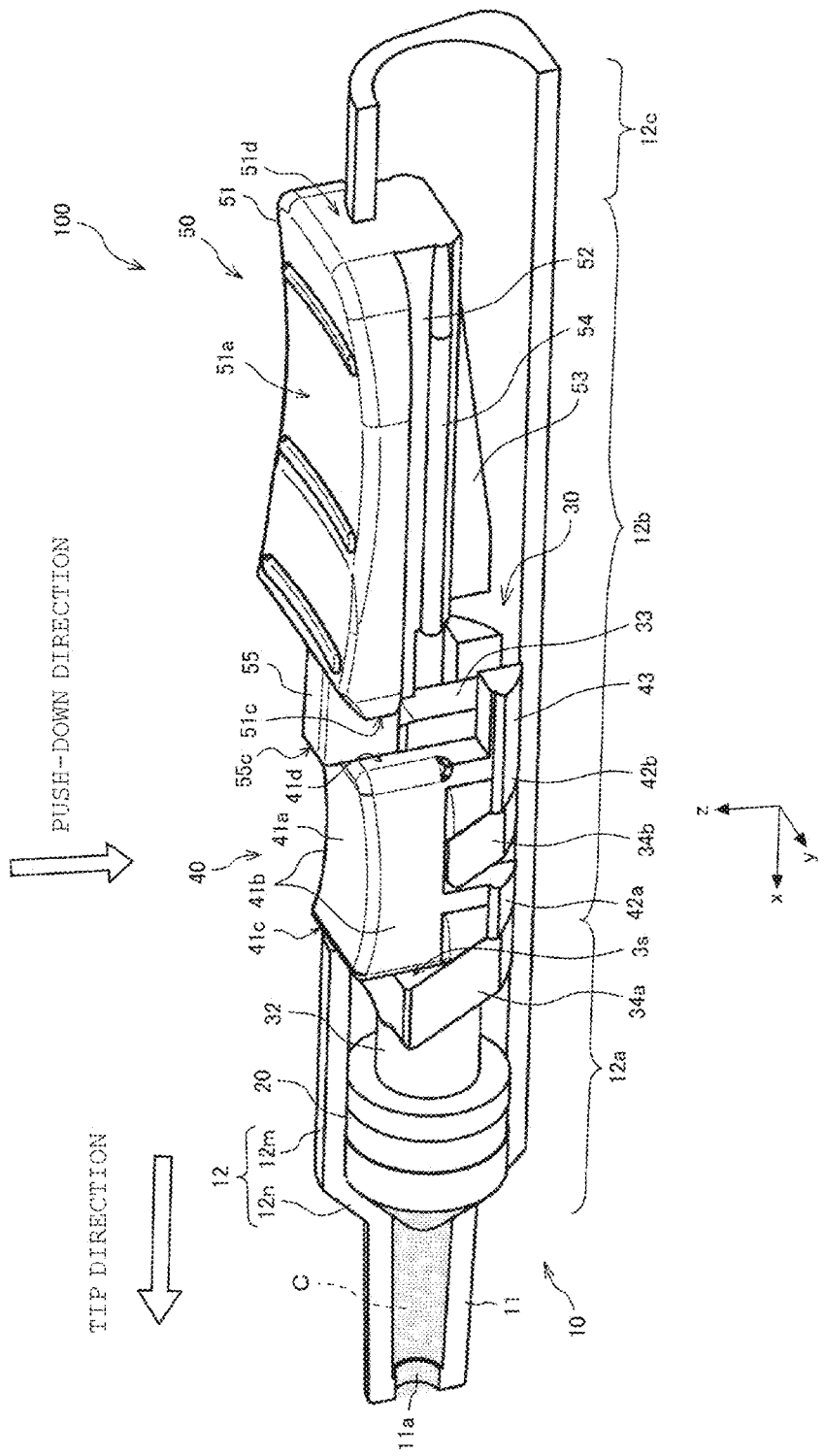
FIG. 11 is a drawing illustrating the injection completion state of the injection device in FIG. 1.

As with FIG. 1, FIG. 8 shows the injection device 100 put in the initial state. FIG. 9 shows the injection device 100 put in a push-out state, which is a state in which the slider 50 is in contact with the button 40 disposed in the frontmost position in the opening 15. In FIG. 9, the button 40 is in contact with both the front wall 15c of the opening 15 and the push end surface 51c of the slider 50. FIG. 10 shows the injection device 100 put in the stretched state. FIG. 11 shows the injection device 100 put in an injection completion state, which is a state in which the button 40 is pushed down in the stretched state of FIG. 10.

When the slider 50 is slid in the tip direction in the injection device 100 put in the initial state (FIG. 8), the conversion portion 30 and button 40 also slide in the tip direction. Then, as seen in the push-out state of FIG. 9, the push-out mechanism stops moving with the button 40 contacting the front wall 15c of the opening 15. In the transition from FIG. 8 to FIG. 9, the gasket 20 moves in the tip direction along with the conversion portion 30 by the length Te (see FIG. 3). That is, the user is able to remove air by operating the slider 50 so that the injection device 100 makes the transition from the initial state to the push-out state. Hereafter, the transition from the initial state to the push-out state is also referred to as "air removal."

In the injection device 100 put in the push-out state (FIG. 9), the preset prescribed amount of chemical solution C remains in the chemical solution storage portion 12a. When the slider 50 is slid rearward in the injection device 100 put in the push-out state, the slider 50 alone moves rearward. When the slider 50 contacts the rear wall 15d of the opening 15, it stops moving, as seen in the stretched state of FIG. 10. At this time, the safety protrusion 55 is gradually removed from the pinching groove 45.

In the injection device 100 put in the stretched state (FIG. 10), the tip end surface 55c of the safety protrusion 55 is flush with the rear end surface 41d of the button 40. Thus, the user is able to push down the button 40 along the tip end surface 55c of the safety protrusion 55. After the safety protrusion 55 is removed from the pinching groove 45, the position of the button 40 is maintained mainly by the static friction between the front slopes 4s and the rear slopes 3s of the conversion portion 30 and the static friction between the gasket 20 connected to the conversion portion 30 and the syringe 10.

When the button 40 is pushed down in the injection device 100 in the stretched state, the movement in the push-down direction of the button 40 is converted into movement in the tip direction by the conversion portion 30 and the gasket 20 moves toward the front end of the body 12. When the button 40 is pushed down to the maximum extent possible (by the stroke H) in the injection device 100 according to the first embodiment, the gasket 20 contacts the tip portion of the body 12 and the prescribed amount of chemical solution C is injected from the injection needle mounted on the cylinder tip portion 11 into the injection subject or the like, as shown in FIG. 11.

Next, referring to FIGS. 12 and 13, the stroke H, the amount of movement L, the set angle θ, the inner diameter D (mm) of the body 12, the diameter α (mm) of the protruding portions 4m, the width W (mm) of the button 40, and the prescribed amount (dose) of chemical solution C, and the relationships therebetween will be described. The amount of movement L is the distance of movement in the tip direction of the gasket 20 when the button 40 is pushed down to the maximum extent possible. While the cross-sectional shape of the protruding portions 4m is approximately a circular shape herein, it is not limited to such a shape.

Figure 12:
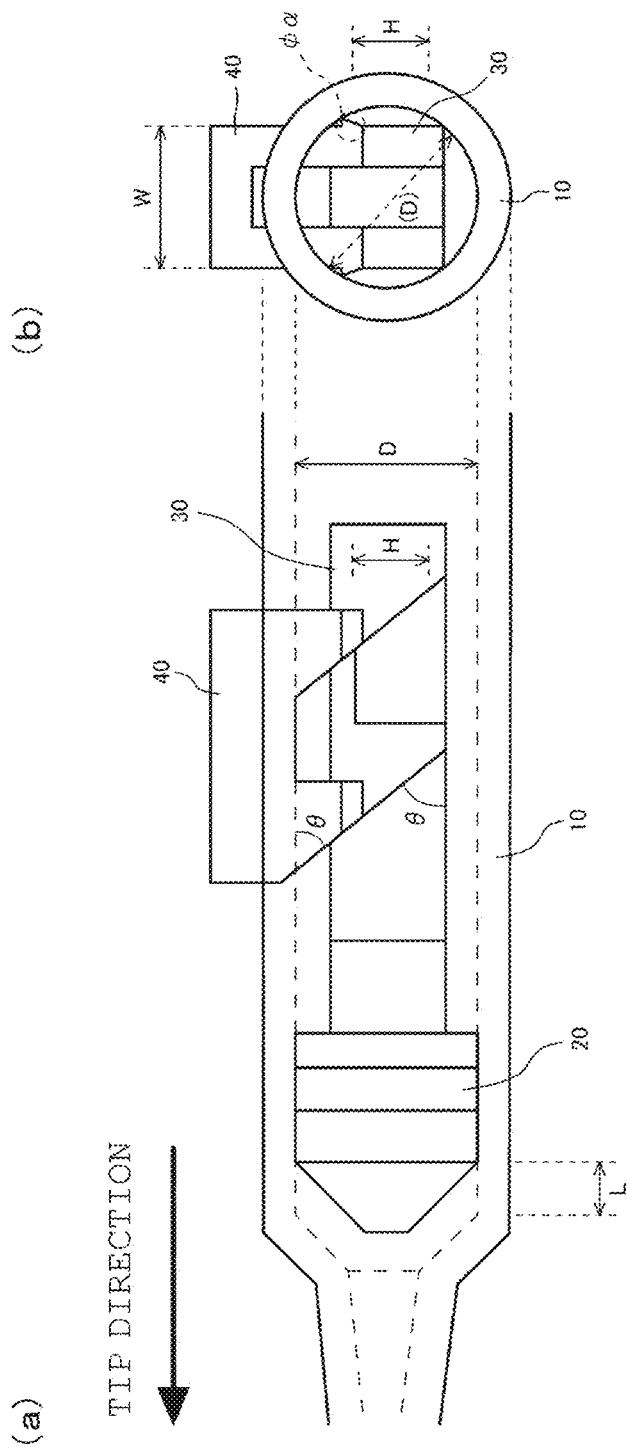
FIG. 12A is a drawing schematically illustrating a left side view of the configuration of the injection device in FIG. 1 focused on a conversion portion and the button.
FIG. 12B is a drawing schematically illustrating a rear view of the configuration of the injection device in FIG. 1 focused on a conversion portion and the button.

As is understood from FIG. 12, the set angle θ, the stroke H, and the amount of movement L have a relationship of "tan θ=H/L". This is arranged as the following Formula (1) with respect to the set angle θ.

[Formula 1]

$$\theta = \arctan(H/L) \quad \quad (1)$$

Figure 13:
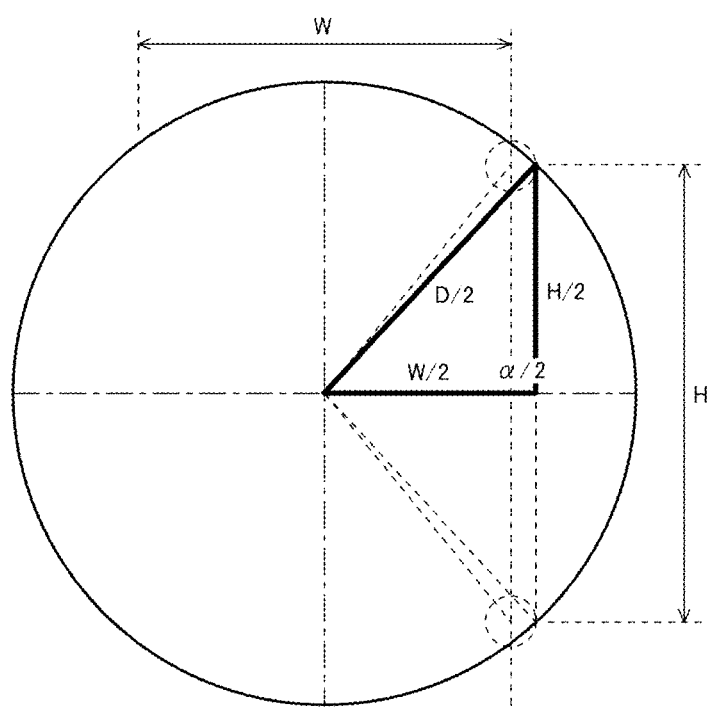
FIG. 13 is a schematic view showing the relationships between the inner diameter of the body, the width of the button, the diameter of a protruding portion, and a stroke assuming the injection device in FIG. 1.

Assuming that the lengths of the components are those shown in FIG. 13, the relationship between the lengths is represented as "$(W/2+\alpha/2)^2+(H/2)^2 \approx (D/2)^2$" on the basis of the Pythagorean theorem. This is arranged as the following Formula (2) with respect to the stroke H. Note that in Formula (2), the square root (√) of the entire "$(D^2-4(W/2+\alpha/2)^2)$" is obtained.

[Formula 2]

-continued $$H = \sqrt{D^2 - 4(W/2 + \alpha/2)^2} \quad \ldots \quad (2)$$

The relationship between the dose V (mm³: μL), the inner diameter D, and the amount of movement L are represented as "V=π×(D/2)²×L". This is arranged as the following Formula (3) with respect to the amount of movement L.

[Formula 3]

$$L = 4V/(\pi D^2) \quad \ldots \quad (3)$$

It is preferable to adjust the settings of the above parameters in consideration of the sense of resistance when the button 40 is pushed down, the certainty of push-down of the button 40, the amount of movement L, the dose V, or the like. As the set angle θ is increased, the resistance when the button 40 is pushed down is reduced. For this reason, as the set angle θ is increased, the user is able to inject the chemical solution C with a lighter touch. Note that when the set angle θ is increased excessively, the amount of movement L is reduced and thus the dose of the chemical solution C is reduced. In the first embodiment, the set angle θ is set in the range of, for example, 45° to 65°. However, the set angle θ may be arbitrarily adjusted to an angle inside or outside the above range in accordance with the size of the entire injection device, the dose of the chemical solution C, or the like. The same also applies to second and third embodiments.

As described above, the injection device 100 includes the conversion portion 30 contained in the body 12, the button 40 supported by the conversion portion 30 with the side portions thereof sandwiched between the side walls 15b of the opening 15, and the slider 50 for moving the conversion portion 30 and button 40 in the tip direction. The button 40 includes the pair of leg portions 42 having the front slopes 4s, and the conversion portion 30 includes the pair of engaging portions 34 having the rear slopes 3s that slidingly contact the front slopes 4s of the button 40. Thus, the user is able to remove air by operating the slider 50 located on a side portion of the body 12 so that the conversion portion 30 is moved in the tip direction. The user is also able to inject the liquid to the injection subject by operating the button 40 located on a side portion of the body 12 so that the conversion portion 30 is further moved in the tip direction. This eliminates frequent switching of the injection device area to be held from the series of operations related to injection and reduces the load on the injection subject.

In the case of a conventional injection device, a predetermined force is required to push down a plunger. This and the needle position and the operation area being away from each other are more likely to cause an injection device shake. An injection device shake during injection may cause a shift in the position of the needle after the needle is punctured and may damage the punctured portion or its vicinity. In the case of the injection device 100, the user only has to perform a simple operation of pushing down the button 40 and thus is able to move the conversion portion 30 connected to the gasket 20 in the tip direction and to inject the chemical solution C into the body of a human or animal, or the like. In the case of the injection device 100, the user is able to push the button 40 using only the index finger. Thus, the user is able to support the injection device 100 using the remaining fingers and thus to operate the injection device 100 stably.

The button 40 according to the first embodiment has the pinching groove 45 formed along the tip direction from the rear end surface 41d. The slider 50 includes the safety protrusion 50 disposed on the button 40 side of the operation portion 51 and formed so as to be insertable into the pinching groove 45 of the button 40. Thus, in a state in which the safety protrusion 55 is inserted in the pinching groove 45, the user is prevented from pushing down the button 40. Thus, before performing injection, for example, during air removal, misoperation such as push-down of the button 40 and thus ejection of the chemical solution C is prevented.

The pinching groove 45 according to the first embodiment is formed from the rear end surface 41d of the button 40 to the front end surface 41c. Thus, after the slider 50 moves rearward and the safety protrusion 55 is removed, the bottom 45u of the pinching groove 45 is opposed to the core portion 33, that is, the core portion 33 becomes insertable into the pinching groove 45. Thus, when a force is applied to the button 40 from above, the core portion 33 is inserted into the pinching groove 45. This allows the user to push down the button 40. That is, the pinching groove 45 prevents misoperation of the button 40, as well as provides the stroke H, which is the distance by which the button 40 can be pushed down, between the pinching groove 45 and the core portion 33.

The safety protrusion 55 is formed such that the tip end surface 55c becomes flush with the rear end surface 41d in a state in which the button 40 is in contact with the front wall 15c of the opening 15 and the slider 50 is in contact with the rear wall 15d of the opening 15. Thus, when the button 40 is pushed down, the button 40 moves in the push-down direction with the rear end surface 41d contacting the tip end surface 55c of the safety protrusion 55. At this time, the slider 50 is prevented from moving rearward by the rear wall 15d of the opening 15. Thus, the button 40 is pushed down while being prevented from moving rearward by the safety protrusion 55. Thus, the operation in the push-down direction of the button 40 is converted into operation in the tip direction of the conversion portion 30 as it is, and the user is able to surely inject the prescribed amount of chemical solution C charged into the chemical solution storage portion 12a into the human body or the like.

The slider 50 may include the operation portion 51 formed such that the width Ws becomes wider than the width (W₂) of the opening 15, the pinching portion 52 connected to the operation portion 51 and disposed between the side walls 15b of the opening 15, and the auxiliary portion 53 connected to the pinching portion 52 and disposed inside the body 12. The auxiliary portion 53 may include the pair of protruding portions 54 formed along the tip direction so as to contact the inner wall 12r of the body 12. Thus, the side walls 15b of the opening 15 are sandwiched between both side end portions of the operation portion 51 and the pair of protruding portions 54 while being opposed to the pinching portion 52. Thus, the opening 15 serves as a rail for causing the slider 50 to smoothly slide in the front-rear direction. The slider 50 is prevented from falling down from the syringe 10 by the pair of protruding portions 54.

The auxiliary portion 53 may be formed such that a step is formed between the auxiliary portion 53 and the pinching portion 52 on the button 40 side. The pair of leg portions 42 may include the first leg portions 42a disposed on the gasket 20 side and the second leg portions 42b disposed on the slider 50 side. The button 40 may include the pair of come-out prevention portions 43 that extend rearward from lower portions of the second leg portions 42b and are to be engaged with the bottom portion 52b of the pinching portion 52. Fall-down of the slider 50 is suppressed by the pair of protruding portions 54, and the button 40 put in the initial state and the push-out state is disposed such that the come-out prevention portions 43 are opposed to the bottom portion 52b of the pinching portion 52. Thus, fall-down of the button 40 is more surely prevented.

The opening 15 becomes wider in the tip direction from the position of the rear end surface 41d of the button 40 in contact with the front wall 15c. That is, the steps 15s are formed in positions of the rear end surface 41d of the button 40 in contact with the front wall 15c on the side walls 15b of the opening 15. Thus, when the button 40 moves in the tip direction in accordance with an operation on the slider 50, it moves from a narrower portion (width $W_2$) to a wider portion (width $W_1$) of the opening 15. The button 40 that has entered the region having the width $W_2$ is prevented from moving rearward by the steps 15s, which are narrower rearward. Thus, when the user contacts the button 40 with the front wall 15c and then moves the slider 50 rearward, the user is able to avoid a situation in which the button 40 moves rearward in conjunction with the movement of the slider 50.

The pair of leg portions 42 each include the base portions 4a extending from the side walls 41b. The base portions 4a may have the depressions 4k in the tip direction-side positions thereof adjacent to the side walls 15b of the opening 15. Since the front-side resistance of the base portions 4a is reduced by the depressions 4k, the button 40 smoothly moves in the tip direction. Also, the rear-side resistance of the base portions 4a is relatively increased due to the presence of the depressions 4k. This suppresses rearward movement of the button 40.

The pair of leg portions 42 may each include the base portions 4a extending from the side walls 41b and the fitting portions 4b extending from the base portions 4a. The fitting portions 4b have a curved shape in which the opposed surfaces 4r disposed so as to be opposed to the inner wall 12r of the body are along the inner wall 12r of the body 12. This shape provides a longer core 33-side length to the fitting portions 4b. Thus, in a state in which the button 40 has yet to be pushed down, the pair of leg portions 42 and the core portion 33 overlap each other over a greater range. Thus, the placement stability of the button 40 is increased. Also, the fitting portions 4b are tapered inwardly and have a predetermined length in the up-down direction on the core portion 33 side, as shown in FIG. 6. However, the shape of the opposed surfaces 4r is along the inner wall 12r. Thus, the maximum stroke H is ensured while maintaining placement stability.

<Modification A>

Figure 14:
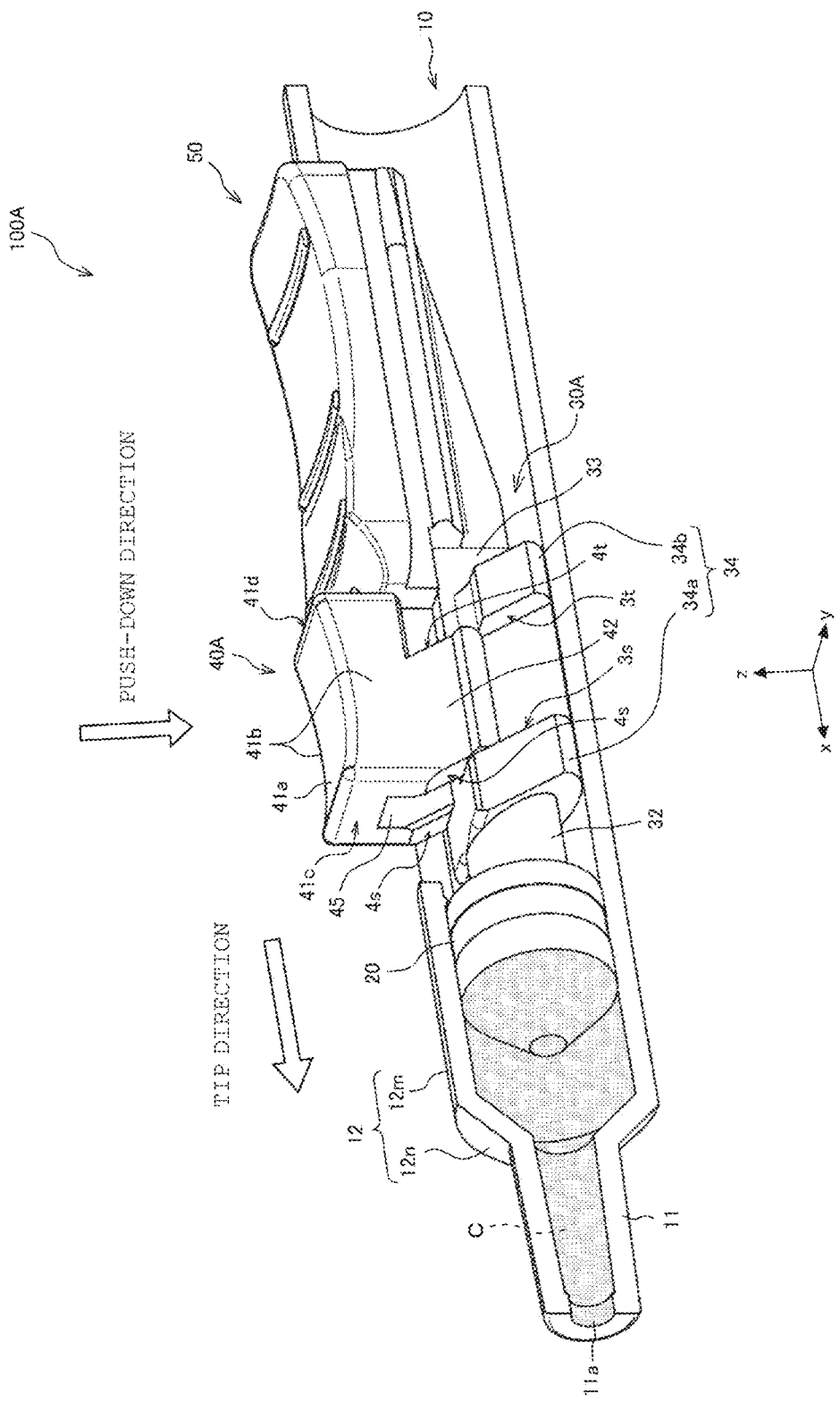
FIG. 14 is a perspective view showing an example configuration of an injection device according to a modification A of the first embodiment of the present invention.

Referring to FIG. 14, an injection device 100A according to a modification A of the first embodiment will be described. Components similar to those of the injection device 100 are given the same reference signs, and the description thereof will be omitted or simplified. In the injection device 100A according to the modification A, the pair of leg portions 42 of a button 40A have front slopes 4s inclined with respect to the tip direction by a set angle θ and rear auxiliary slopes 4t inclined with respect to the tip direction by the set angle θ. Thus, the leg portions 42 have a parallelogram shape in a side view. The front slopes 4s are disposed on the front side of the leg portions 42, and the rear auxiliary slopes 4t are disposed on the rear side of the leg portions 42.

Also, in the injection device 100A, the pair of engaging portions 34 of a conversion portion 30A each include a first engaging portion 34a and a second engaging portion 34b. The first engaging portion 34a has a rear slope 3s that slidingly contacts the front slope 4s of one leg portion 42. The second engaging portion 34b according to the modification A has a front auxiliary slope 3t that slidingly contacts the rear auxiliary slopes 4t of the leg portion 42.

The other configurations of the conversion portion 30A and button 40A are similar to those of the conversion portion 30 and button 40 described above. The syringe 10, gasket 20, and slider 50 of the injection device 100A are similar to those of the injection device 100. The configurations and alternative configurations of the injection device 100 can be applied to the injection device 100A.

By configuring an injection device such that the leg portions 42 of the button 40A are sandwiched between the first engaging portions 34a and second engaging portions 34b of the conversion portion 30A, as seen in the injection device 100A, the button 40A is stably supported even if each leg portion 42 is not divided into two portions, that is, a front portion and a rear portion. That is, in the injection device 100A, the leg portions 42 of the button 40A slide in groovy portions between the first engaging portions 34a and second engaging portions 34b. That is, the first engaging portions 34a and second engaging portions 34b serve as rails for guiding the leg portions 42 when the user pushes down the button 40A. Thus, the user is able to smoothly and stably operate the button 40A. Other advantageous effects and the like are similar to those of the injection device 100.

<Modification B>

Figure 15:
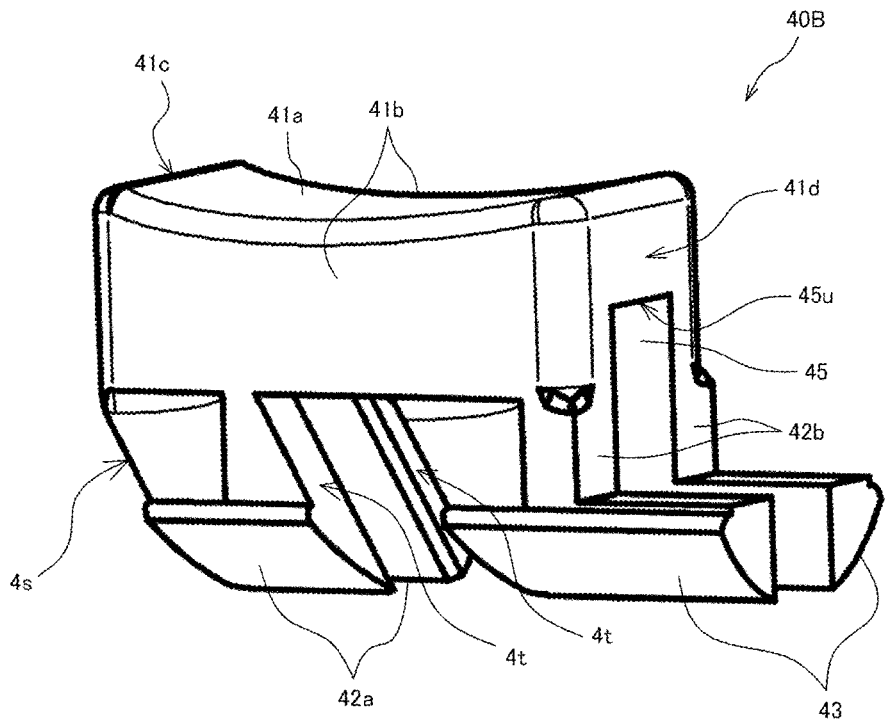
FIG. 15 is a perspective view illustrating the button of an injection device according to a modification B of the first embodiment of the present invention.

Referring to FIG. 15, the configuration of the button 40B of an injection device 100 according to a modification B of the first embodiment will be described. The syringe 10, gasket 20, conversion portion 30, and slider 50 of the injection device 100 according to the modification B are similar to those of the above injection device 100. Note that the conversion portion 30 is required to have front auxiliary slopes 3t inclined with respect to the tip direction by a set angle θ, as shown in an example in FIG. 2. Components similar to the above button 40 and button 40A are given the same reference signs, and the description thereof will be omitted or simplified.

In the button 40B of the injection device 100 according to the modification B, the first leg portions 42a of a pair of leg portions 42 have front slopes 4s that slidingly contact the rear slopes 3s of the conversion portion 30 and rear auxiliary slopes 4t that slidingly contact the front auxiliary slopes 3t (see FIG. 2) of the conversion portion 30. That is, the first leg portions 42a have a parallelogram shape in a side view. Thus, both sides of the first leg portions 42a of the button 40B are sandwiched between the first engaging portions 34a and second engaging portions 34b of the conversion portion 30. Thus, the button 40B is stably supported by the conversion portion 30. Thus, the operation stability of the button 40B is increased. Other advantageous effects and the like are similar to those of the injection device 100 according to the first embodiment and the injection device 100A according to the modification A.

<Modification C>

Figure 16:
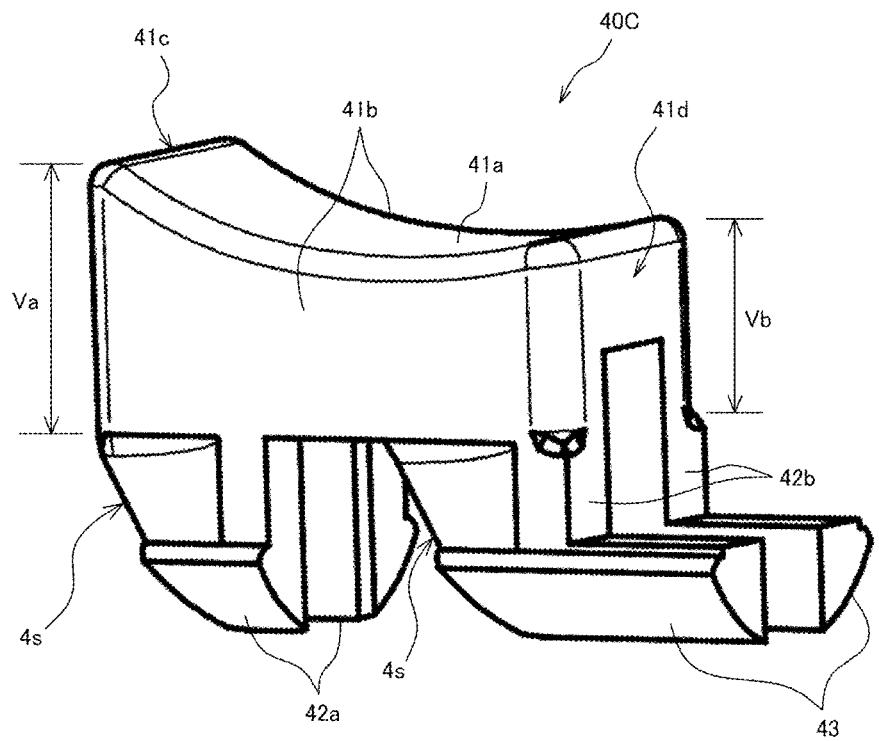
FIG. 16 is a perspective view illustrating the button of an injection device according to a modification C of the first embodiment of the present invention.

Referring to FIG. 16, the configuration of the button 40C of an injection device 100 according to a modification C of the first embodiment will be described. The syringe 10, gasket 20, conversion portion 30, and slider 50 of the injection device 100 according to the modification C are similar to those of the above injection devices 100. Components similar to the buttons 40, 40A, and 40B are given the same reference signs, and the description thereof will be omitted or simplified.

In the case of the button 40C according to the modification C, the length Vb in the push-down direction of the rear end surface 41d is shorter than the length Va in the push-down direction of the front end surface 41c. A face wall 41a has a downward curved shape. Thus, a user is able to push down the button 40C with a natural touch even if the user does not consciously vertically push the button 40C. That is, the user is able to smoothly and easily operate the button 40C. It is preferable to set the difference between the length Va and the length Vb in accordance with the size of the entire injection device 100, the stroke H, the amount of movement L, or the like. While FIG. 16 shows an example in which the face wall 41a is formed so as to be downward curved, this example is not limiting. For example, the face wall 41a may have a shape having a recessed central portion, or may be a flat slope. The configuration of the button 40C according to the modification C may be applied to the button 40A according to the modification A, or may be applied to the button 40B according to the modification B.

Second Embodiment

Referring to FIGS. 17 to 24, an example configuration of an injection device 400 according to a second embodiment will be described. To clearly show the operating state of a push-out mechanism, FIGS. 17 and 20 to 24 illustrate a syringe 10 whose half is cut off. In these drawings, the area into which a chemical solution C is charged is dotted so that the movement of the chemical solution C is clarified. Components similar to those of the first embodiment are given the same reference signs, and the description thereof will be omitted or simplified.

Figure 17:
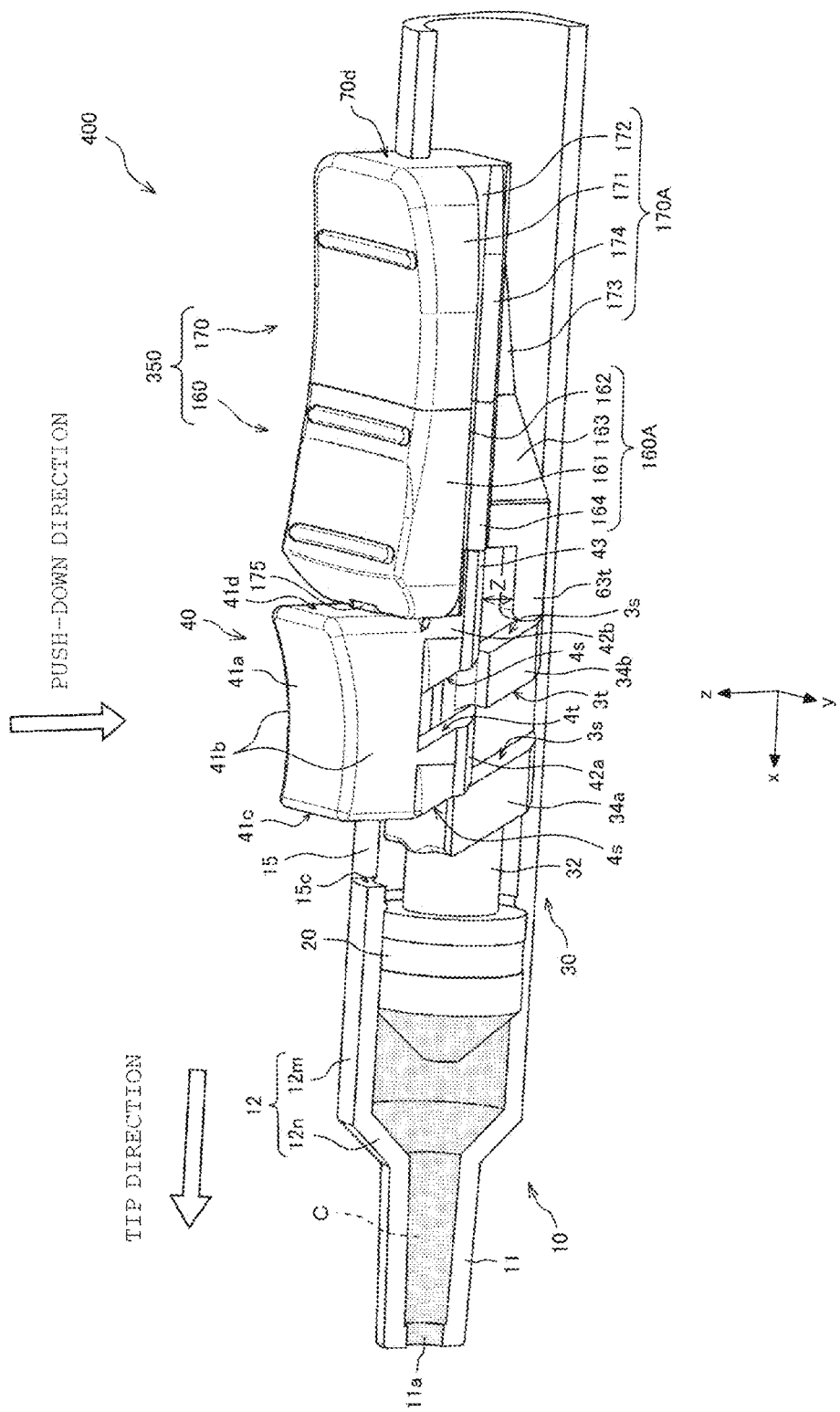
FIG. 17 is a drawing showing an example configuration (initial state) of an injection device according to a second embodiment of the present invention.

FIG. 17 is a drawing illustrating the initial state of the injection device 400. As shown in FIG. 17, the injection device 400 includes the syringe 10, a gasket 20, a conversion portion 30, a button 40, and a slider 350. The slider 350 includes a first slider 160 disposed one the button 40 side and a second slider 170 disposed near the rear wall 15d of an opening 15. The initial state shown in FIG. 17 is a state in which the second slider 170 is in contact with the rear wall 15d of the opening 15 and the button 40 is in contact with the push end surface 51c of the first slider 160. The button 40 in the drawings has a configuration similar to that of the button 40B according to the modification B, and the length Vb in the push-down direction of the rear end surface 41d is longer than the length Va in the push-down direction of the front end surface 41c. The button 40 is not limited to the example configuration in the drawings and may have a configuration similar to those of the buttons 40 and 40A to 40C disclosed in the first embodiment.

The first slider 160 includes a first body 160A having a communication hole 65h (see FIG. 18) extending from the push end surface 51c, which is a front end surface, to a rear end surface 60d. The first body 160A includes a first operation portion 161 having a wider width than the width (W₂) of the opening 15, and a first sandwiched portion 162 disposed between both side walls 15b of the opening 15, and a first auxiliary portion 163 disposed inside a body 12. The first auxiliary portion 163 includes a pair of protruding portions 164 formed along the tip direction so as to contact the inner wall 12r of the body 12. The shape of the protruding portions 164 is similar to that of the protruding portions 54 according to the first embodiment.

The first slider 160 includes a limitation protrusion 165 extending in the tip direction from the first body 160A and formed so as to be insertable into the pinching groove 45 of the button 40. The first auxiliary portion 163 illustrated in the drawings includes a pair of auxiliary protrusions 63 formed so as to correspond to the pair of come-out prevention portions 43 of the button 40 and extending forward from lower portions of the first auxiliary portion 163. The tip end surface 65c of the limitation protrusion 165 is flush with the rear end surface 41d of the button 40 in a state in which the button 40 is disposed in the frontmost position in the opening 15 and the first slider 160 and second slider 170 are disposed in the rearmost position in the opening 15 (see FIGS. 23 and 24). The limitation protrusion 165 illustrated in the drawings is connected to the first operation portion 161 and first sandwiched portion 162.

The second slider 170 includes a second body 170A disposed outside the body 12 and including a second operation portion 171 formed so as to have a wider width than the width (W₂) of the opening 15. The second body 170A includes a second sandwiched portion 172 disposed between the side walls 15b of the opening 15 and a second auxiliary portion 173 disposed inside the body 12. The second auxiliary portion 173 includes a pair of protruding portions 174 formed along the tip direction so as to contact the inner wall 12r of the body 12. The shape of the protruding portions 174 is similar to that of the protruding portions 54 according to the first embodiment.

The second slider 170 includes a safety protrusion 175 disposed on the button 40 side of the second operation portion 171 and formed so as to be insertable into the communication hole 65h and pinching groove 45. The tip portion 75n of the safety protrusion 175 is disposed on the limitation protrusion 165 in a state in which the second slider 170 is in contact with the rear end surface 60d of the first slider 160 (see FIGS. 23 and 24). The tip end surface 75c of the limitation protrusion 175 is flush with the rear end surface 41d of the button 40 in a state in which the button 40 is disposed in the frontmost position in the opening 15 and the second slider 170 are disposed in the rearmost position in the opening 15 (see FIGS. 21 to 24).

Figure 18:
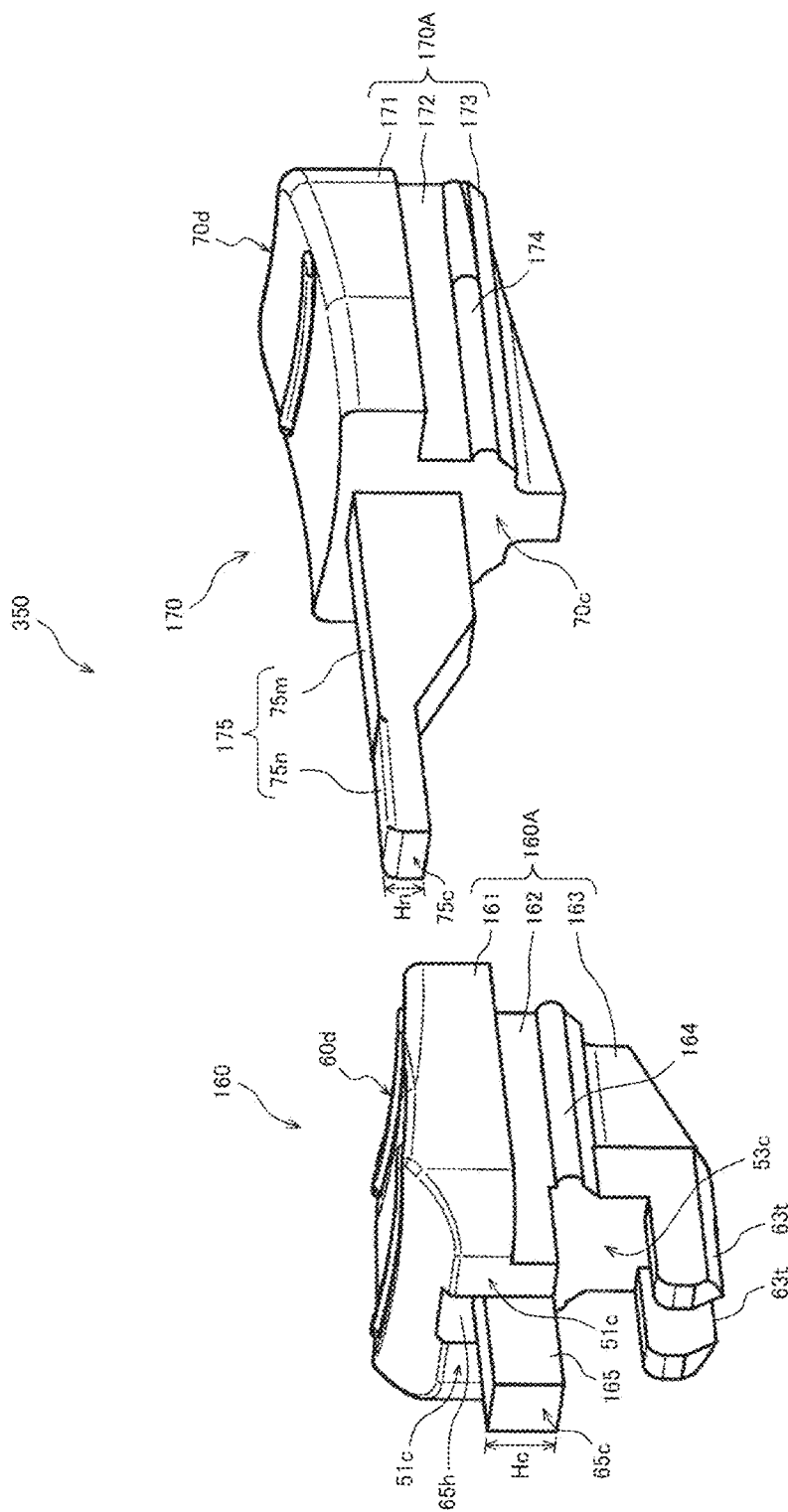
FIG. 18 is an exploded perspective view illustrating the individual members of a slider in FIG. 17.
Figure 19:
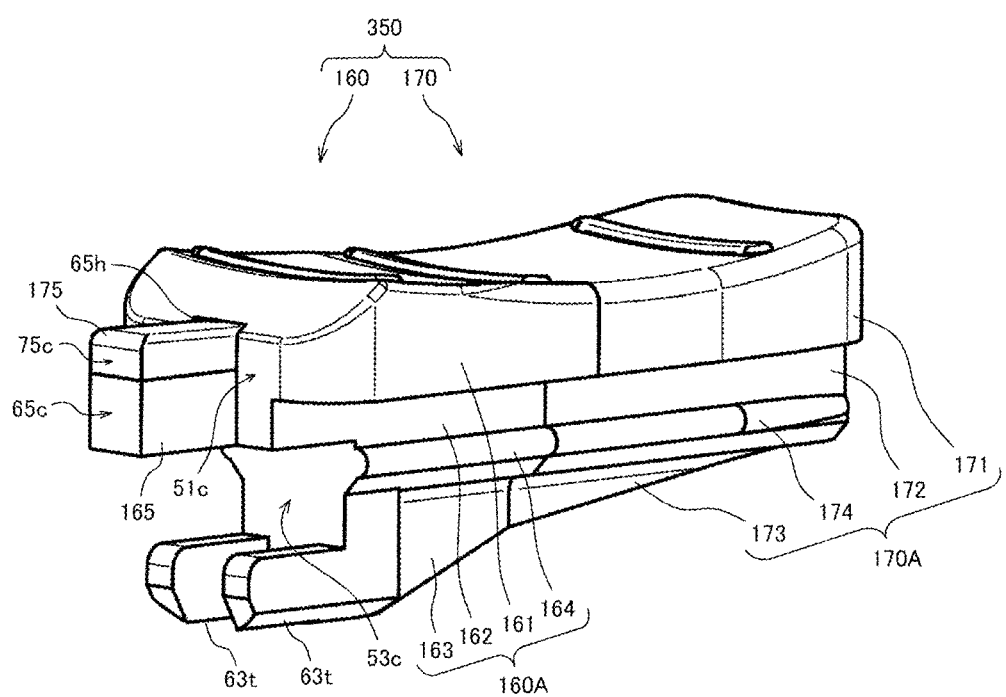
FIG. 19 is a perspective view showing an example of a state in which a first slider and a second slider in FIG. 18 are combined.

Hereafter, referring to FIGS. 18 and 19, the specific configuration of the first slider 160 and second slider 170 will be further described. FIG. 19 shows a contact state, which is a state in which the safety protrusion 175 is inserted in the communication hole 65h and the rear end surface 60d of the first slider 160 and the contact end surface 70c of the second slider 170 are in contact with each other. The contact end surface 70c is the front end surface of the second body 170A.

As shown in FIG. 18, the safety protrusion 175 includes a base portion 75m extending forward from the contact end surface 70c of the second body 170A and the tip portion 75n extending forward from the base portion 75m. In the contact state, the tip portion 75n is disposed on the limitation protrusion 165. As illustrated in FIG. 19, in the contact state, the tip end surface 75c of the tip portion 75n according to the second embodiment is flush with the tip end surface 65c of the limitation protrusion 165.

The height Hn of the tip portion 75n is set in accordance with a preset initial action dose. The initial action dose is set in accordance with the type of the chemical solution C, or the like and can be changed as necessary. In the second embodiment, the auxiliary protrusions 63t of the first slider 160 are formed such that the distance Z from the lower ends of the come-out prevention portions 43 to the auxiliary protrusions 63t (see FIGS. 17, 20, and 21) becomes equal to the height Hn of the tip portion 75n in the initial state or the like. It is preferable to set the height Hc of the limitation protrusion 165 in consideration of the operation stability of the button 40.

Figure 20:
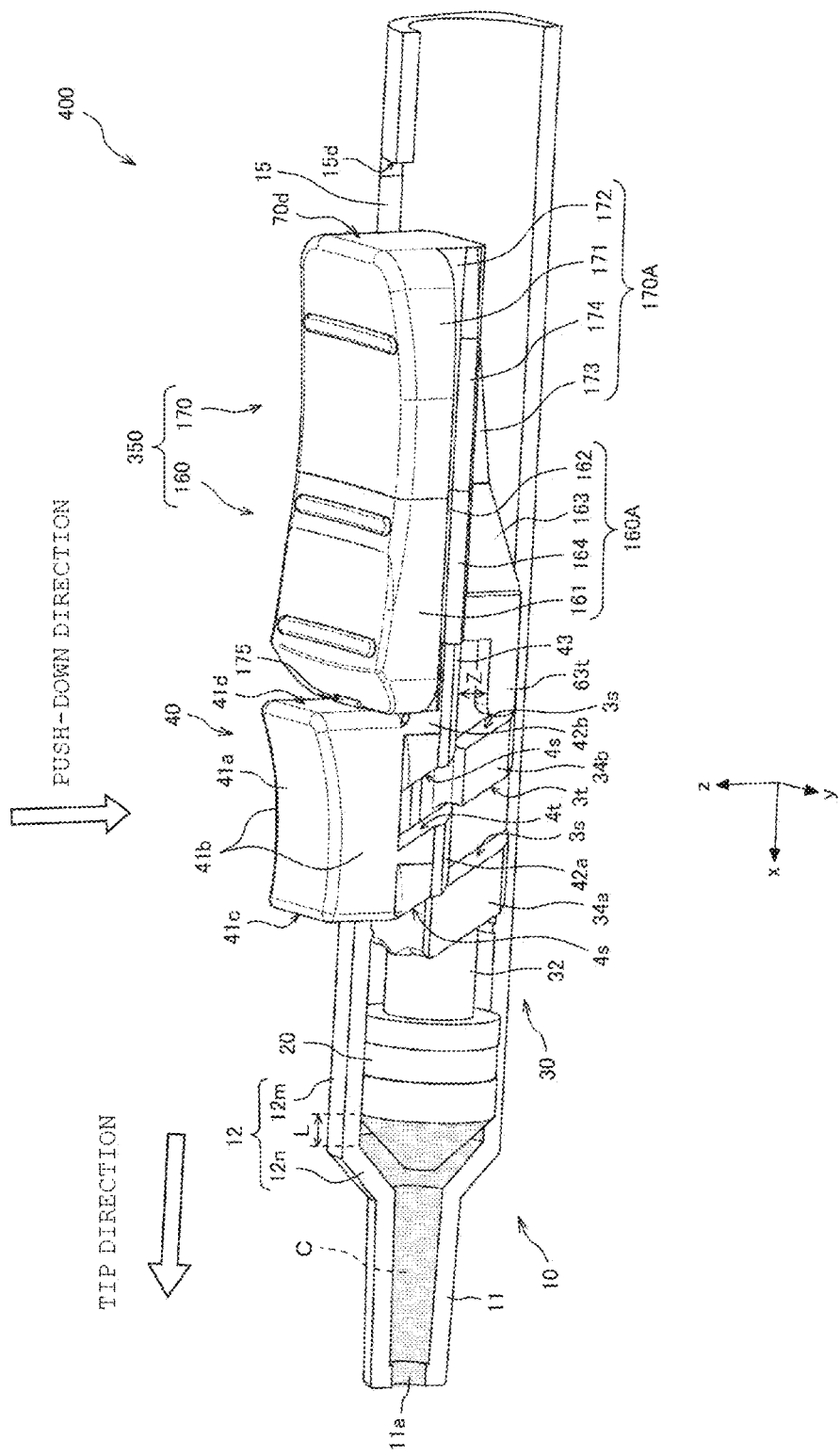
FIG. 20 is a drawing illustrating the push-out state of the injection device in FIG. 17.
Figure 21:
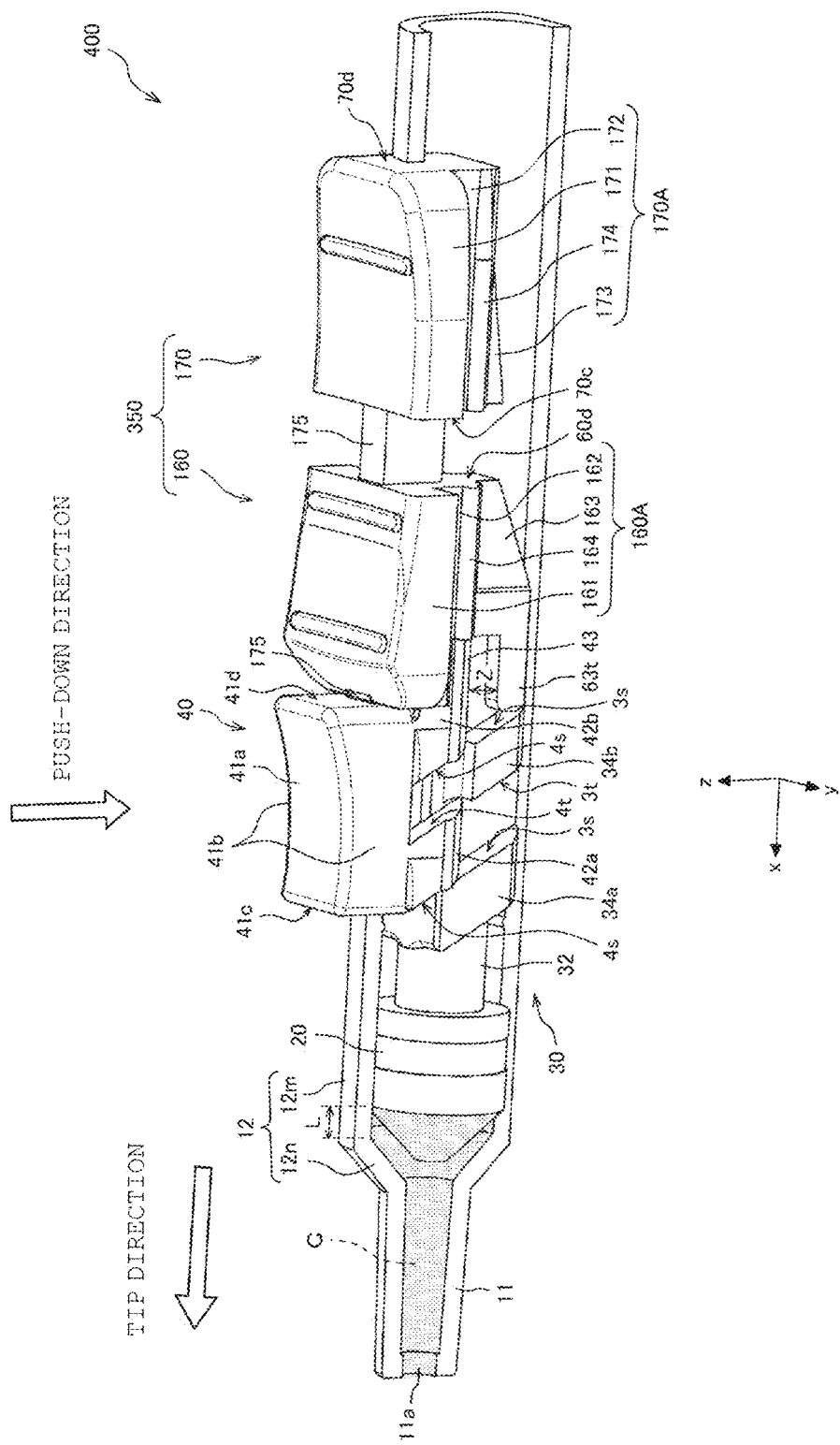
FIG. 21 is a drawing illustrating the first stretched state of the injection device in FIG. 17.
Figure 22:
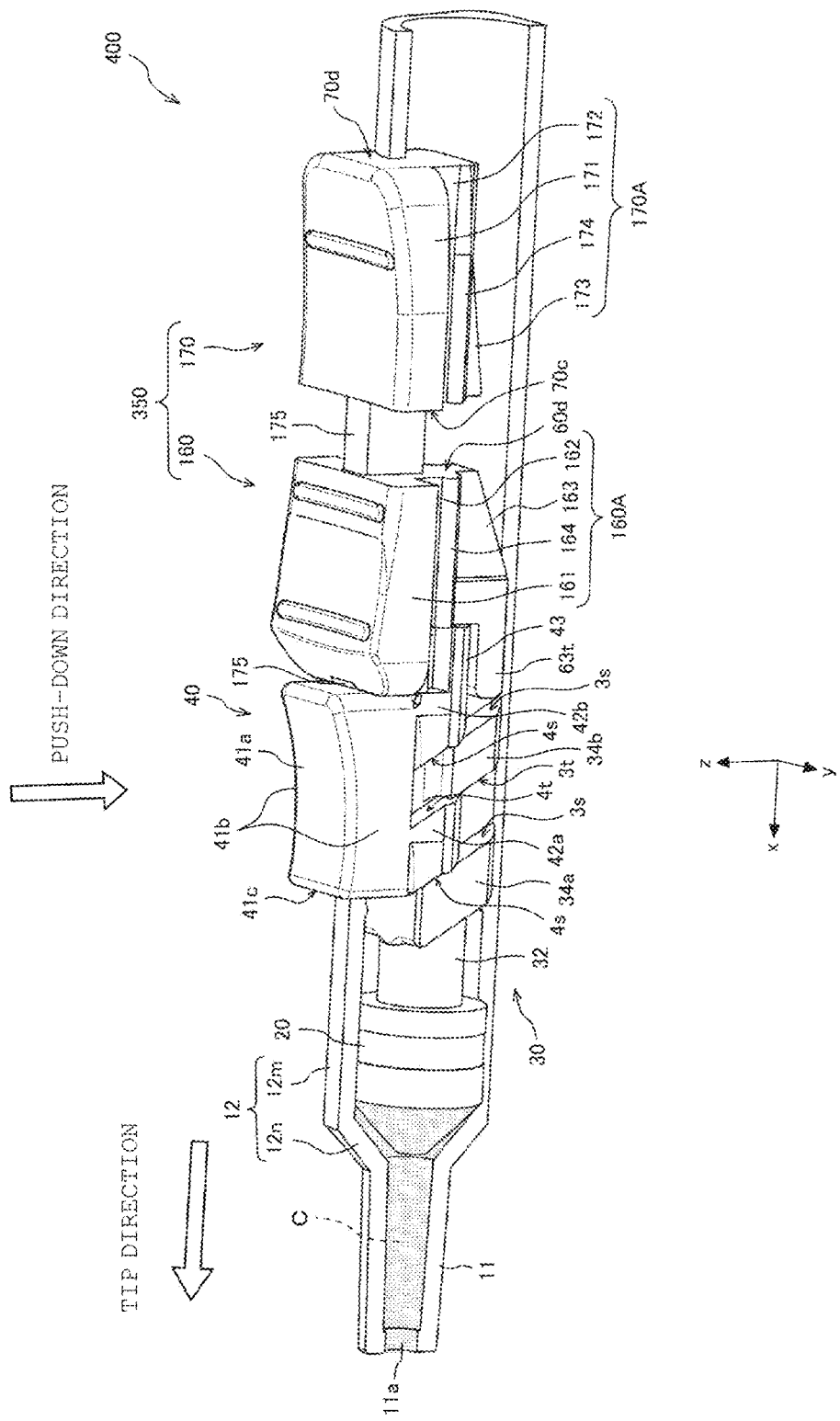
FIG. 22 is a drawing illustrating the first push-down state of the injection device in FIG. 17.
Figure 23:
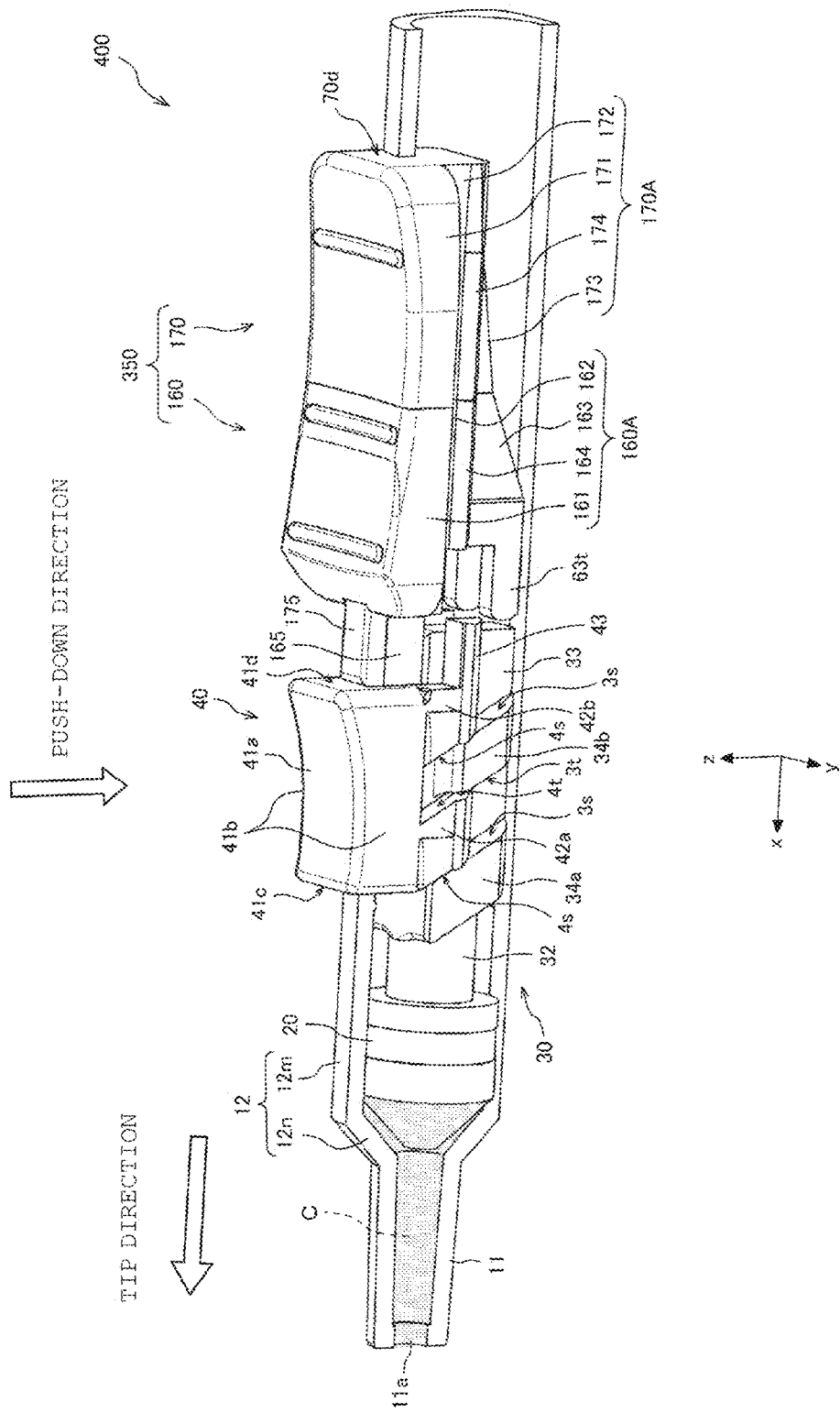
FIG. 23 is a drawing illustrating the second stretched state of the injection device in FIG. 17.
Figure 24:
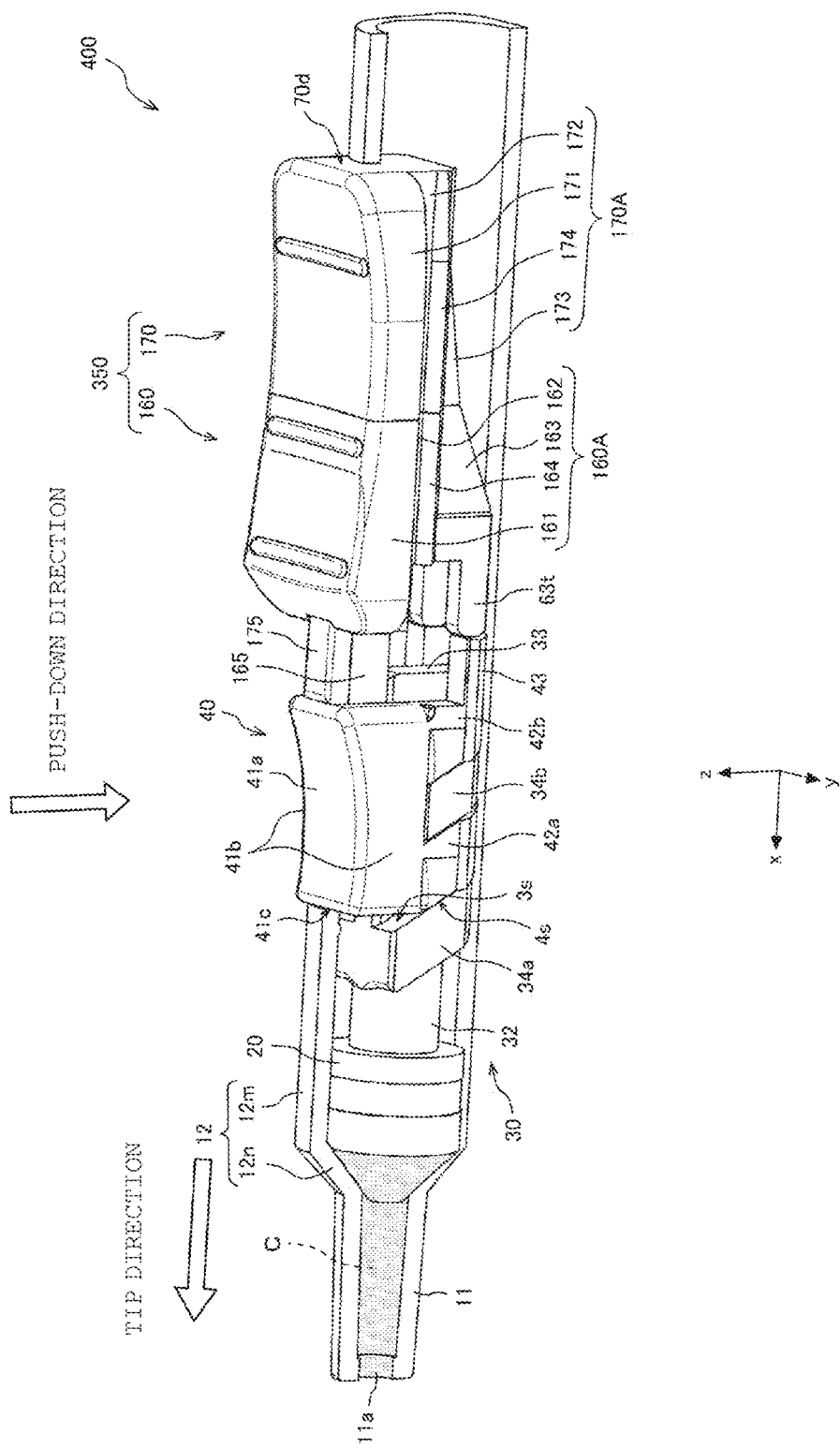
FIG. 24 is a drawing illustrating the second push-down state of the injection device in FIG. 17.

Next, referring to FIGS. 17 and 20 to 24, a series of operations related to injection using the injection device 400 will be described. FIG. 20 shows the injection device 400 put in the push-out state. The push-out state is a state in which the button 40 disposed in the frontmost position in the opening 15 is in contact with the push end surface 51c of the slider 350 put in the contact state. FIG. 21 shows the injection device 400 put in a first stretched state. The first stretched state is a state in which the button 40 disposed in the frontmost position in the opening 15 is in contact with the push end surface 51c of the slider 350 put in a separated state. The separated state of the slider 350 is a state in which the rear end surface 60d and the contact end surface 70c are not in contact with each other and the push end surface 51c of the first slider 160 and the tip end surface 75c of the safety protrusion 175 are flush with each other. FIG. 22 shows the injection device 400 put in a first push-down state, which is a state in which the button 40 is pushed down in the first stretched state. FIG. 23 shows the injection device 400 put in a second stretched state. The second stretched state is a state in which the button 40 is disposed in the frontmost position in the opening 15 and the slider 350 put in the contact state is disposed in the rearmost position in the opening 15. In the second embodiment, the rearmost position in the opening 15 of the slider 350 put in the contact state is the position in which the rear end surface 70d of the second slider 170 is in contact with the rear wall 15d. FIG. 24 shows the injection device 400 in a second push-down state, which is a state in which the button 40 is pushed down in the second stretched state.

In the push-out state shown in FIG. 20, the button 40 is in contact with the front wall 15c of the opening 15. A user is able to remove air by operating the slider 350 so that the injection device 400 makes transition from the initial state to the push-out state. When the user slides the second slider 170 rearward in the injection device 400 put in the push-out state, the tip portion 75n of the safety protrusion 175 is gradually removed from the pinching groove 45. As seen in the first stretched state shown in FIG. 21, when the second slider 170 contacts the rear wall 15d, the tip portion 75n is completely removed from the pinching groove 45.

As seen above, in the injection device 400 put in the first stretched state, there is a gap having a width corresponding to the height Hn of the tip portion 75n between the bottom 45u of the pinching groove 45 and the limitation protrusion 165 of the first slider 160. Thus, the user is able to push down the button 40 along the push end surface 51c until the bottom 45u contacts the limitation protrusion 165 and to put the injection device 400 into the first push-down state shown in FIG. 22. When the button 40 is pushed down by the height Hn, the gasket 20 moves toward the tip of the body 12 by "Hn/tan θ." In an example in FIG. 22, the lower ends of the come-out prevention portions 43 are in contact with the upper ends of the auxiliary protrusions 63t. That is, in the first stretched state of the injection device 400, the auxiliary protrusions 63t serve as auxiliary limiters to the push-down operation of the button 40.

When the user slides the first slider 160 rearward in the injection device 400 put in the first push-down state, the limitation protrusion 165 is gradually removed from the pinching groove 45 and the area in which the upper ends of the auxiliary protrusions 63t and the lower ends of the come-out prevention portions 43 are opposed to each other is gradually reduced. As seen in the second stretched state shown in FIG. 23, when the first slider 160 contacts the second slider 170, the limitation protrusion 165 is completely removed from the pinching groove 45 and the come-out prevention portions 43 and auxiliary protrusions 63t are no longer opposed to each other.

In the injection device 400 put in the second stretched state, the tip end surface 65c of the limitation protrusion 165 is flush with the rear end surface 41d of the button 40. Thus, the user is able to move the button 40 along the tip end surface 65c in the push-down direction and to put the injection device 400 into the second push-down state shown in FIG. 24. In the second stretched state of the injection device 400, the tip end surface 75c of the tip portion 75n is flush with the rear end surface 41d of the button 40. Thus, the user is able to more stably push down the button 40. The user is able to push down the button 40 by the stroke H by performing the operation related to the transition from the first stretched state to the first push-down state and the operation related to the transition from the second stretched state to the second push-down state. That is, by using the injection device 400, the user is able to inject the prescribed amount of chemical solution C into an injection subject or the like in two stages.

As shown in FIG. 23, the injection device 400 put in the second stretched state may be configured such that the rear ends of the come-out prevention portions 43 and the front ends of the auxiliary protrusions 63t are flush with each other. Thus, the area in which the button 40 and slider 350 contact each other is increased, and the button 40 is supported also from below. Thus, the stability of the button 40 during operation is further increased.

As described above, the injection device 400 includes the conversion portion 30 contained in the body 12, the button 40 supported by the conversion portion 30 with the side portions thereof sandwiched between the side walls 15b of the opening 15, and the slider 350 for moving the conversion portion 30 and button 40 in the tip direction. Thus, the user is able to remove air by operating the slider 350 located on a side portion of the body 12. The user is also able to inject the liquid to the injection subject by operating the button 40 located on a side portion of the body 12 so that the conversion portion 30 is further moved in the tip direction. This eliminates frequent switching of the injection device area to be held from the series of operations related to injection and reduces the load on the injection subject.

The slider 350 according to the second embodiment includes the first slider 160 and second slider 170. The first slider 160 includes the first body 160A having the communication hole 65h and the limitation protrusion 165 formed so as to be insertable into the pinching groove 45. The second slider 170 includes the safety protrusion 175 formed so as to be insertable into the communication hole 65h and pinching groove 45. The tip portion 75n of the safety protrusion 175 is disposed on the limitation protrusion 165 in a state in which the second slider 170 is in contact with the rear end surface 60d of the first slider 160. Thus, as seen in the initial state (FIG. 17) and push-out state (FIG. 20), in a state in which the tip portion 75n is inserted in the pinching groove 45, the user is prevented from pushing down the button 40. Thus, before performing injection, for example, during air removal, misoperation such as push-down of the button 40 and thus ejection of the chemical solution C is prevented.

The safety protrusion 175 is formed such that the tip end surface 75c is flush with the rear end surface 41d of the button 40 in a state in which the button 40 is disposed in the frontmost position in the opening 15 and the second slider 170 are disposed in the rearmost position in the opening 15 (see FIGS. 21 to 24). That is, in the injection device 400 put in the first stretched state (FIG. 21), the limitation protrusion 165 is inserted in the pinching groove 45, and the tip portion 75n is removed from the pinching groove 45. Thus, the injection device 400 put in the first stretched state allows the limitation protrusion 165 to serve as a limiter to the push-down operation of the button 40 and is able to eject the chemical solution in the initial action dose corresponding to the height Hn of the tip portion 75n.

The limitation protrusion 165 is formed such that the tip end surface 65c is flush with the rear end surface 41d of the button 40 in a state in which the button 40 is disposed in the frontmost position in the opening 15 and the first slider 160 and second slider 170 (the slider 350 put in the contact state) are disposed in the rearmost position in the opening 15. That is, in the injection device 400 put in the second stretched state (FIG. 23), the rear end surface 41d of the button 40 is in contact with the tip end surface 65c of the limitation protrusion 165. Also, in the injection device 400 put in the second stretched state, rearward movement of the first slider 160 is blocked by the rear wall 15d of the opening 15 through the second slider 170. Thus, the user is able to move the button 40 in the push-down direction along the tip end surface 65c.

As described above, the injection device 400 is configured to be able to eject the prescribed amount of chemical solution C in two stages. Thus, the user is able to inject the initial action dose of chemical solution C to the injection subject by pushing down the button 40 in the injection device 400 put in the first stretched state, to check the condition of the injection subject, and then to determine whether to inject the remaining chemical solution C. Thus, by using the injection device 400, the user is able to flexibly administer the chemical solution in accordance with the physical condition of the injection subject, or the like. That is, by using the injection device 400, the user is able to administer the chemical solution in two stages, for example, by injecting 20 μL of chemical solution C to the injection subject, then checking the stability of the condition of the injection subject, and then additionally injecting 30 μL of chemical solution C. Other advantageous effects and the like are similar to those of the first embodiment. The configurations and alternative configurations of the injection device 100 according to the first embodiment can be applied to the injection device 400, and the configurations of the modifications A to C can also be applied thereto.

The position in the tip direction of the front wall 15c of the opening 15 is set on the basis of the position of the gasket 20 with the front end surface 41c of the button 40 contacting the front wall 15c, that is, the prescribed amount of chemical solution C. However, the prescribed amount of the chemical solution C is not necessarily constant. For this reason, if the position of the front wall 15c is fixed, it is necessary to produce injection devices for each prescribed amount. For this reason, an adjustment mechanism that can change the range of motion of the buttons 40 and 40A to 40C may be provided on the front wall 15c or its vicinity of the syringe 10 of the injection devices according to the first and second embodiments. The adjustment mechanism allows the user to adjust the position corresponding to the front wall 15c of the opening 15 in the front-rear direction.

The adjustment mechanism may be configured to be able to make stepwise adjustments corresponding to multiple doses, for example, may be configured to be able to set any dose in a sliding manner. The injection device 400 including the adjustment mechanism makes the position of the buttons 40 and 40A to 40C at the time of push-down variable and makes the position of the front wall 15c substantially adjustable. That is, by providing an allowance to the amount of movement L corresponding to the stroke H, the dose of the chemical solution C becomes adjustable.

Third Embodiment

Figure 25:
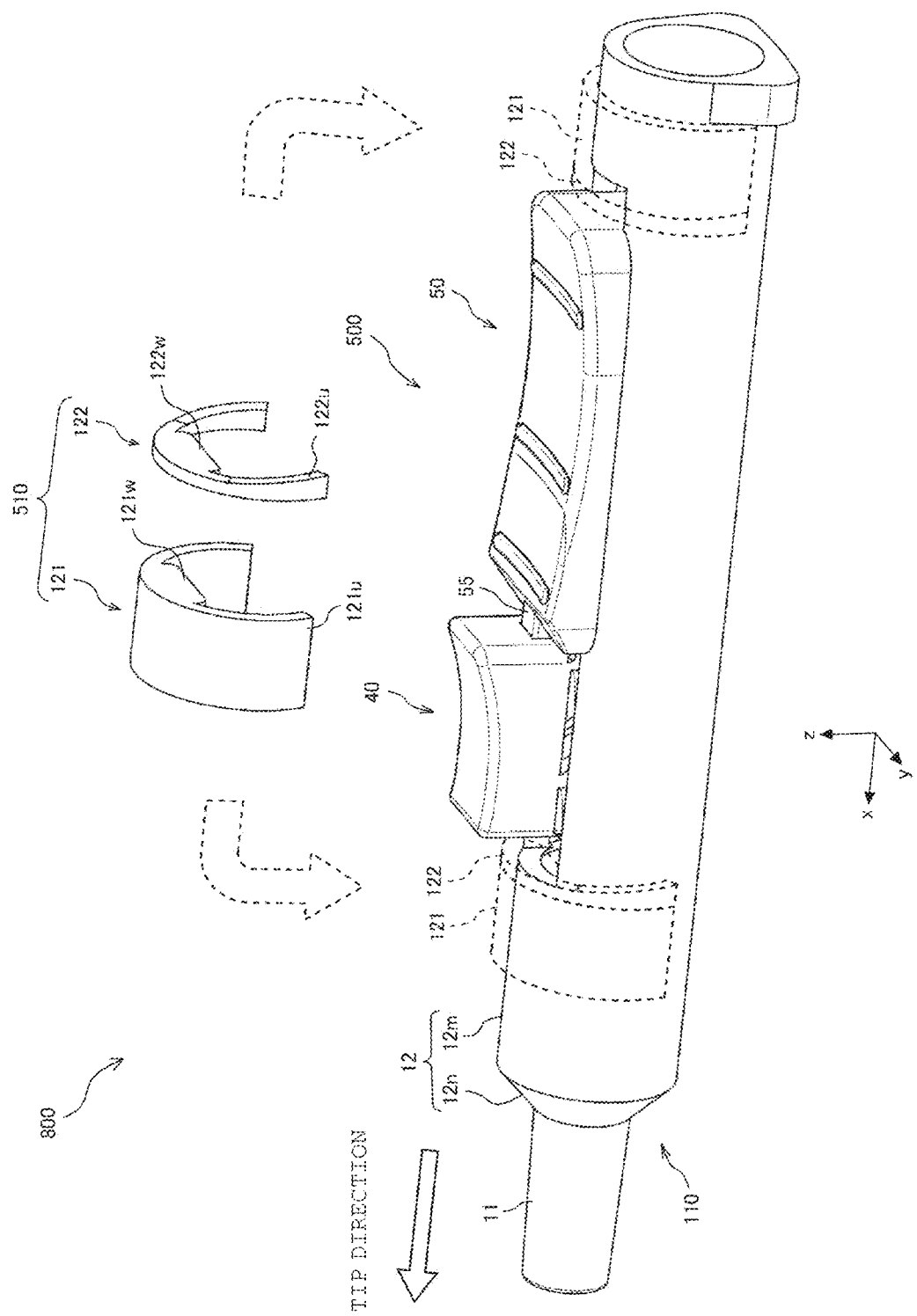
FIG. 25 is a perspective view showing an example configuration of an injection device and injection unit according to a third embodiment of the present invention.
Figure 27:
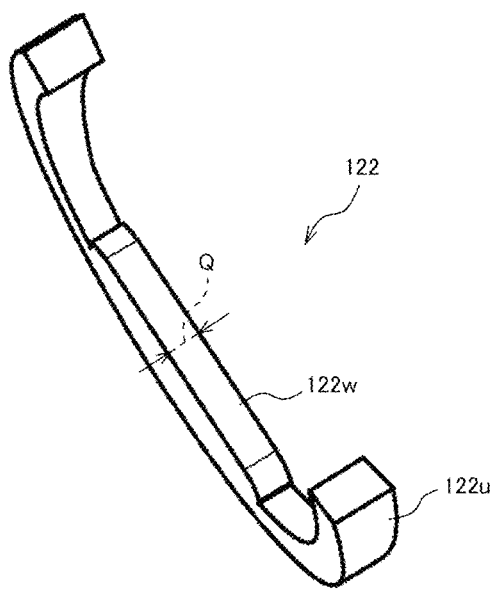
FIG. 27 is a configuration drawing of a second adjustment member in FIG. 25 seen from inside.
Figure 28:
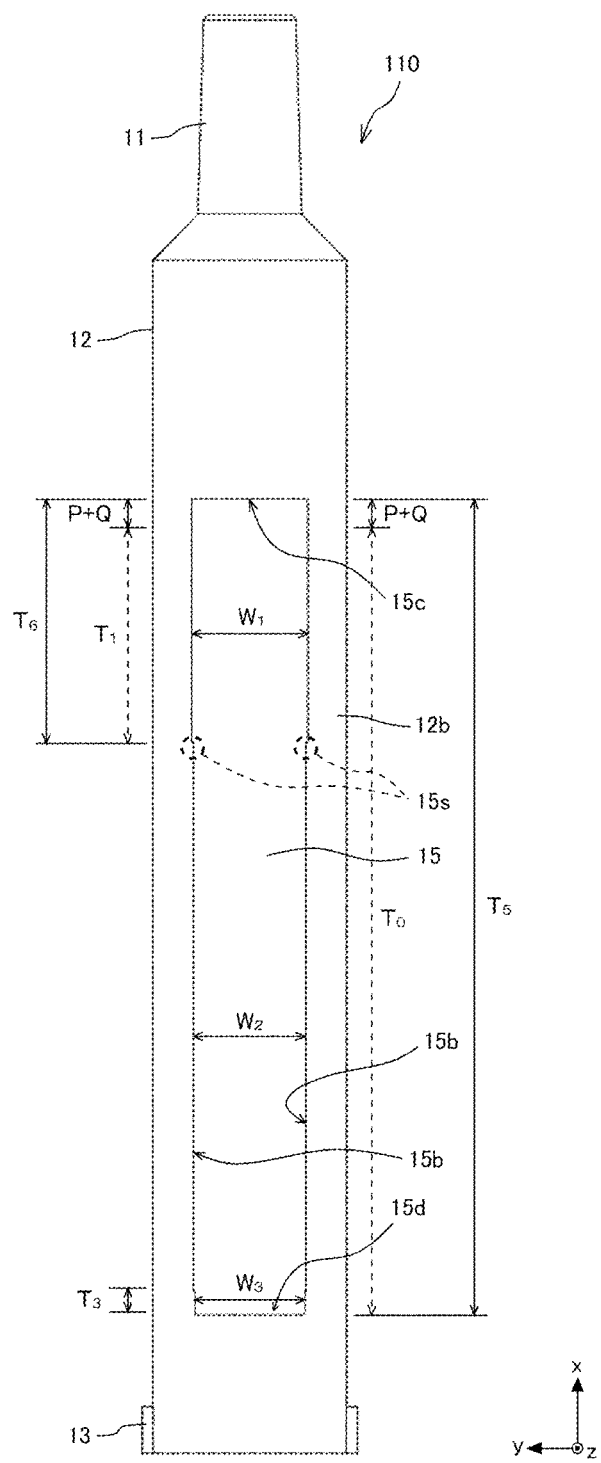
FIG. 28 is a plan view of a syringe in FIG. 25 seen from above.
Figure 29:
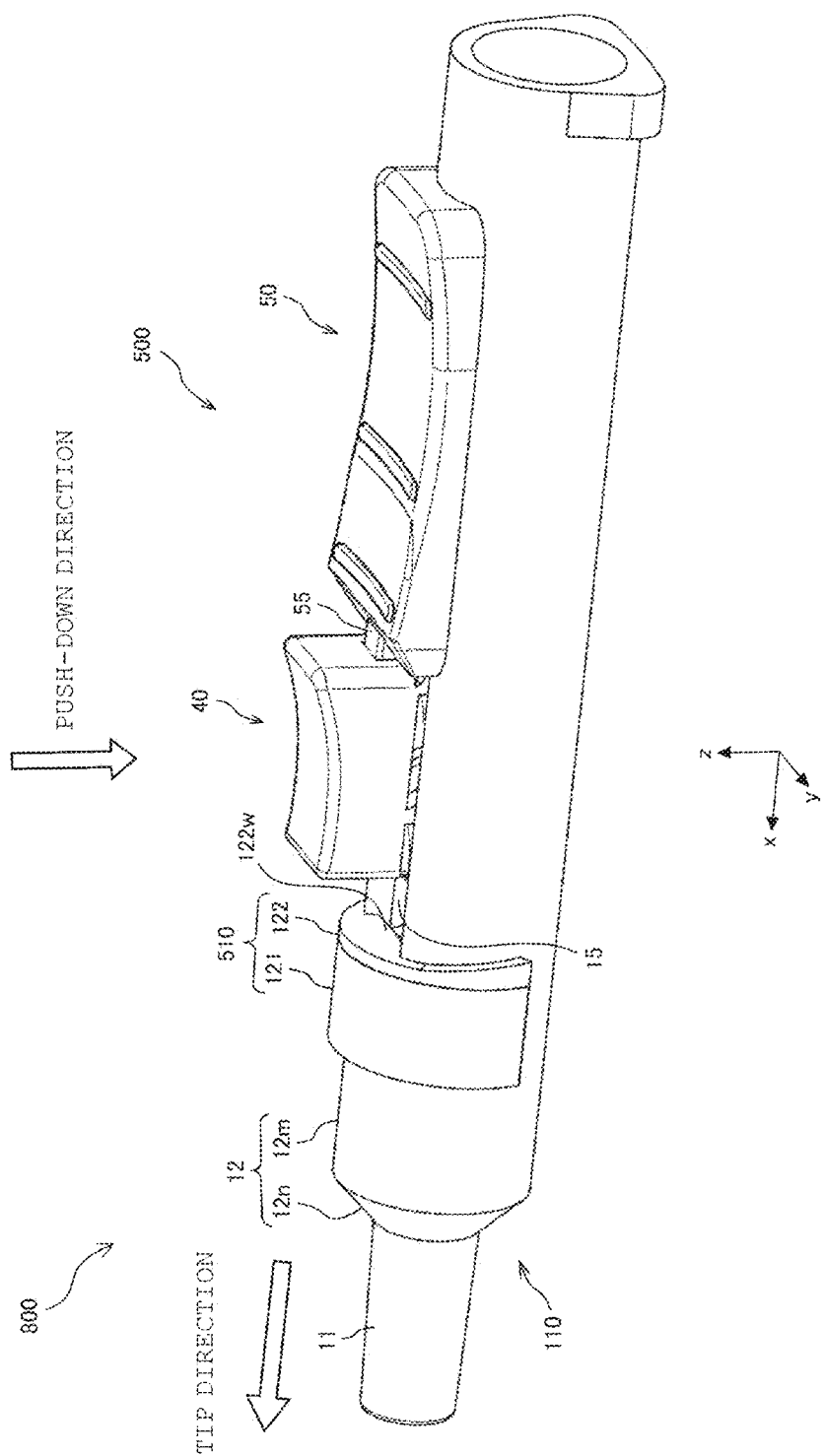
FIG. 29 is a drawing showing an example of the initial state of the injection unit in FIG. 25.

Referring to FIGS. 25 to 33, an example configuration of an injection unit 800 according to a third embodiment will be described. Components similar to those of the first and second embodiment are given the same reference signs, and the description thereof will be omitted or simplified. The injection unit 800 illustrated in these drawings includes an injection device 500 and an adjustment unit 510 configured to adjust the amount of chemical solution C to be ejected from the injection device 500. The injection device 500 includes a syringe 110, a gasket 20, a conversion portion 30, a button 40, and a slider 50. Although the syringe 110 is made of a transparent resin or the like, the internal components and the like are shown in FIGS. 25 and 29 in a non-transparent manner for convenience.

The adjustment unit 510 illustrated in the drawings includes two adjustment members. One adjustment member is referred to as a first adjustment member 121, and the other adjustment member as a second adjustment member 122. As shown in FIG. 25, the first adjustment member 121 includes a frame member 121u having a U-shaped cross-section and a spacer 121w disposed between both side walls 15b of an opening 15. The second adjustment member 122 includes a frame member 122u having a U-shaped cross-section and a spacer 122w disposed between the side walls 15b of the opening 15.

Figure 26:
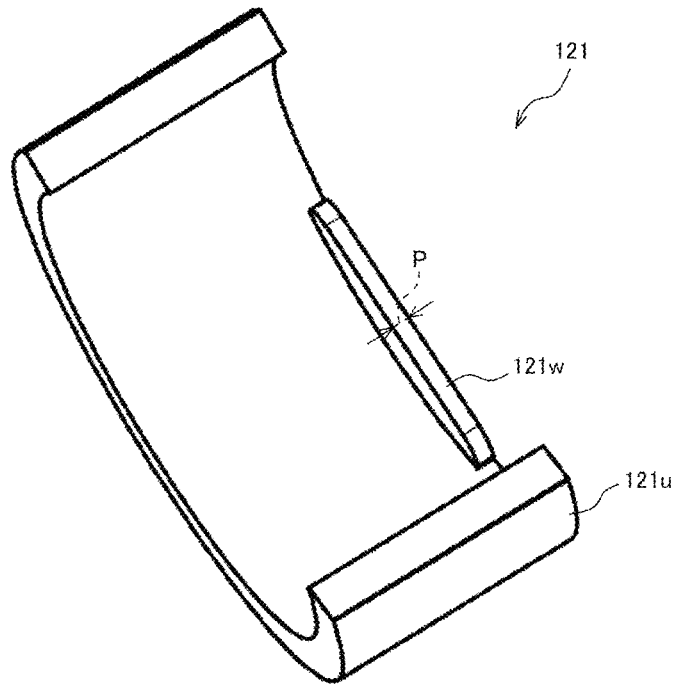
FIG. 26 is a configuration drawing of a first adjustment member in FIG. 25 seen from inside.

The frame member 121u and frame member 122u are formed so as to be along the periphery of the body 12 and are able to pinch the body 12. The spacer 121w is disposed in the central location along the curved direction of the frame member 121u on the inner surface of the frame member 121u. As shown in FIG. 26, the spacer 121w is a plate-shaped member having a width P formed on one end along the tip direction on the inner surface of the frame member 121u. The inner surface of the frame member 121u is a surface oriented toward the body 12 of the frame member 121u. The spacer 122w is disposed in the central location along the curved direction of the frame member 121u on the inner surface of the frame member 122u. As shown in FIG. 27, the spacer 122w is a plate-shaped member having a width Q formed on one end along the tip direction on the inner surface of the frame member 122u. The inner surface of the frame member 122u is a surface oriented toward the body 12 of the frame member 122u. The width P of the spacer 121w is narrower than the width Q of the spacer 122w. The width P and width Q are factors that determine the stepwise amounts of adjustment in the administration of the chemical solution, and can be set arbitrarily and changed. Hereafter, the spacer 121w and spacer 122w may be collectively referred to as spacers 120 without distinguishing them from each other.

As shown by broken lines in FIG. 25, the first adjustment member 121 and second adjustment member 122 can be mounted in a position adjacent to the front wall 15c or a position adjacent to the rear wall 15d of the body 12 with the spacers 120 put in the opening 15. When mounting the first adjustment member 121 adjacent to the front wall 15*c*, the first adjustment member 121 is disposed such that the spacer 121*w* is located on the rear side. When mounting the first adjustment member 121 adjacent to the rear wall 15*d*, the first adjustment member 121 is disposed such that the spacer 121*w* is located on the front side. For this reason, when mounting both the first adjustment member 121 and second adjustment member 122 adjacent to the front wall 15*c*, the first adjustment member 121 is disposed in a more front position than that of the second adjustment member 122. When mounting both the first adjustment member 121 and second adjustment member 122 adjacent to the rear wall 15*d*, the first adjustment member 121 is disposed in a more rear position than that of the second adjustment member 122.

As shown in FIG. 28, the syringe 110 has a configuration similar to that of the syringe 10 according to the first embodiment. Note that the length $T_5$ of the opening 15 of the syringe 110 is longer than the length $T_0$ of the opening 15 of the syringe 10 in FIG. 4 by the sum of the widths of the spacers 120 of the adjustment unit 510, that is, the sum of the width P and width Q ($T_5=T_0+P+Q$). The sum of the widths of the spacers 120 of the adjustment unit 510 is the sum of the widths of the spacers 120 of all the adjustment members of the adjustment unit 510 and is hereafter referred to as the "sum of the widths of the spacers 120." That is, the length $T_5$ is longer than the length from the front end surface 41*c* of the button 40 to the rear end surface 51*d* of the slider 50 by the sum of the widths of the spacers 120 in a state in which the rear end surface 41*d* of the button 40 and the tip end surface 55*c* of the safety protrusion 55 are flush with each other. Also, the length $T_6$ from the front wall 15*c* to the steps 15*s* is longer than the length $T_1$ of the syringe 10 by the sum of the widths of the spacers 120 of the adjustment unit 510.

In the third embodiment, when the adjustment unit 510 is mounted adjacent to the front wall 15*c*, the frontmost position in the opening 15 of the button 40 is a position in contact with the adjustment unit 510. Similarly, when the adjustment unit 510 is mounted adjacent to the rear wall 15*d*, the rearmost position in the opening 15 of the slider 50 is a position in contact with the adjustment unit 510.

Next, referring to FIGS. 29 to 33, a method of adjusting the dose of the chemical solution C by selectively using the adjustment members forming the adjustment unit 510 will be described. The adjustment unit 510 according to the third embodiment includes the two adjustment members including the spacers 120 having different widths. Thus, the dose of the chemical solution C can be adjusted in four stages. For example, as shown in FIG. 29, the initial state of the injection unit 800 is set to a state in which the button 40 and slider 50 are disposed in the rearmost position in the opening 15 and the adjustment unit 510 is mounted adjacent to the front wall 15*c* of the opening 15. By mounting the adjustment members adjacent to the front wall 15*c*, movement in the tip direction of the button 40 is blocked by the spacers 120 thereof during air removal. The gasket 20 moves in conjunction with movement in the tip direction of the button 40 during air removal. For this reason, by mounting more adjustment members adjacent to the front wall 15*c*, a larger amount of chemical solution C can be left in the chemical solution storage portion 12*a* after air removal. Thus, the amount of chemical solution C that can be administered is reduced in stages in the order of FIGS. 30, 31, 32, and 33.

Hereafter, a method for adjusting the dose of the chemical solution C will be described assuming that the injection device 500 is put in the initial state illustrated in FIG. 29. FIGS. 30 to 33 illustrate the injection device 500 put in the stretched state, and the other states are omitted. The stretched state is a state in which the button 40 is located in the placeable frontmost position in the opening 15 and the slider 50 is located in the placeable rearmost position in the opening 15. In the stretched state, the tip end surface 55*c* of the safety protrusion 55 is flush with the rear end surface 41*d*. FIGS. 30 to 33 schematically show the components and illustrate the syringe 10 whose half is cut off. It is assumed that the amount of movement L corresponding to the stroke H has been adjusted in accordance with a state in which the first adjustment member 121 and second adjustment member 122 are mounted adjacent to the front wall 15*c*.

Figure 30:
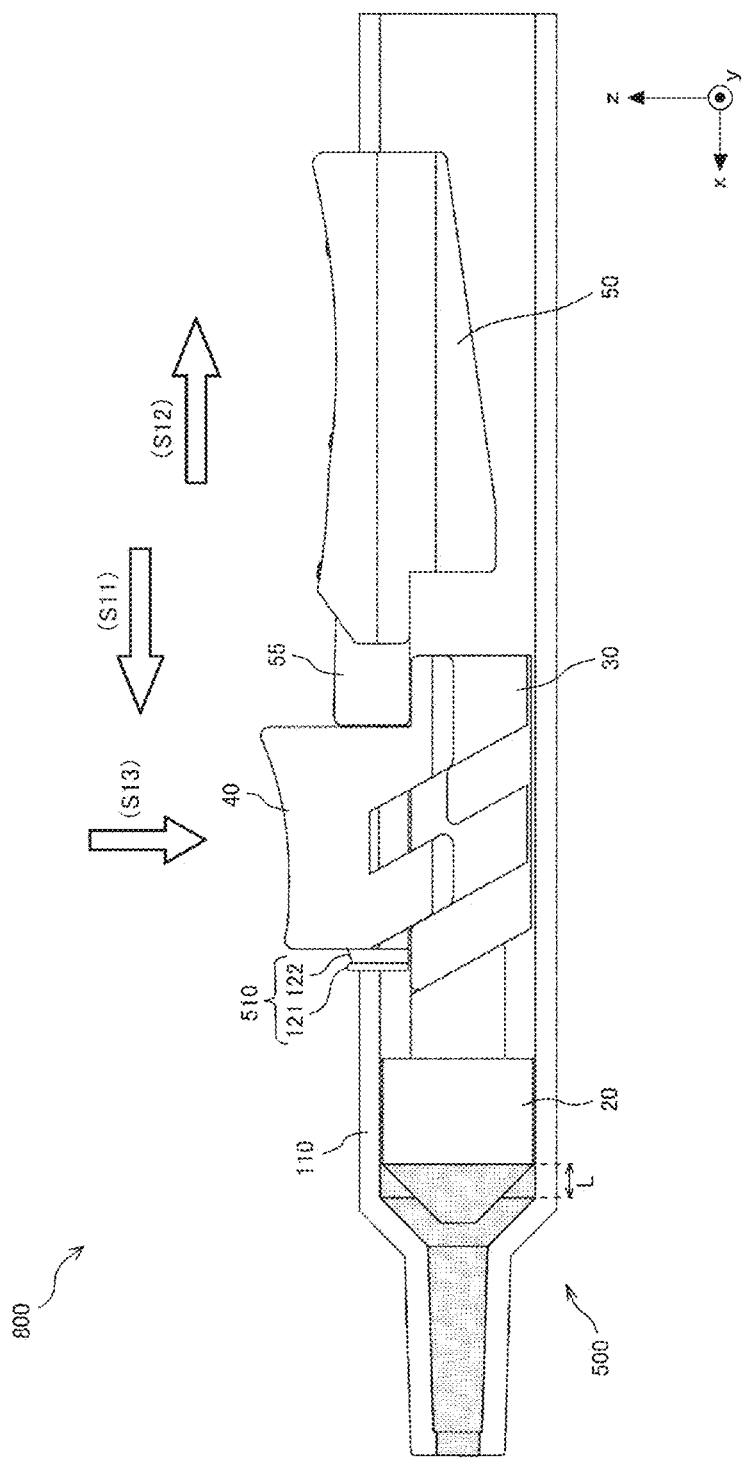
FIG. 30 is a drawing illustrating steps for administering the largest amount of chemical solution from the injection unit in FIG. 25.

FIG. 30 corresponds to a case in which the largest amount of chemical solution C is administered from the injection unit 800. In this case, there is no need to demount the adjustment unit 510 mounted adjacent to the front wall 15*c*. Thus, the user is able to remove air (S11), then to put the injection unit 800 into the stretched state by sliding the slider 50 rearward (S12: the state in FIG. 30), and to inject the chemical solution C corresponding to the amount of movement L to the injection subject or the like by pushing down the button 40 by the stroke H (S13).

Figure 31:
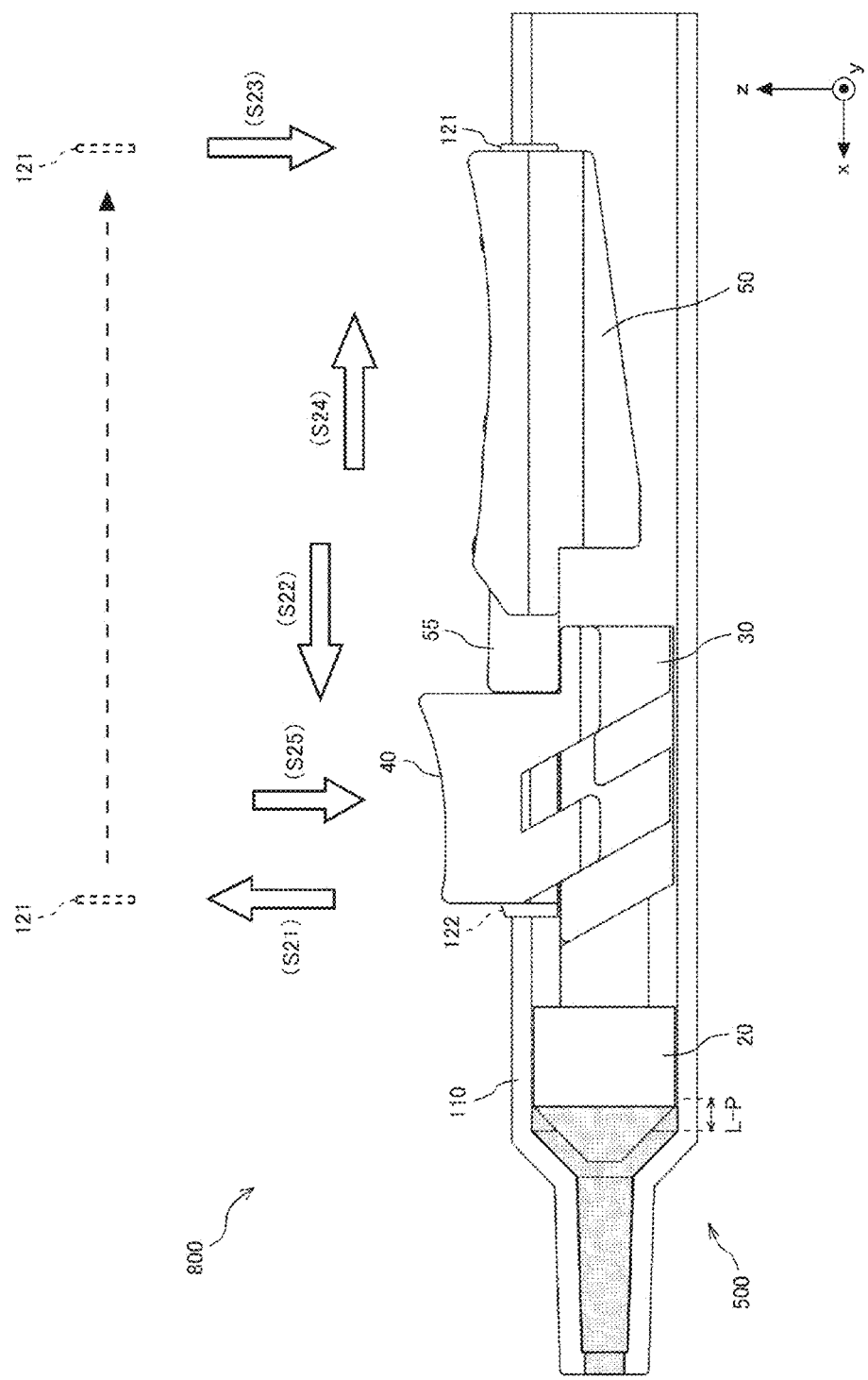
FIG. 31 is a drawing illustrating steps for administering the second largest amount of chemical solution from the injection unit in FIG. 25.

FIG. 31 corresponds to a case in which the second largest amount of chemical solution C, that is, a second amount of chemical solution C is administered from the injection unit 800. In this case, first, the user demounts the first adjustment member 121 mounted adjacent to the front wall 15*c* (S21) and removes air (S22). At this time, the gasket 20 moves forward from the position in FIG. 30 by the width P. Then, the user mounts the first adjustment member 121 adjacent to the rear wall 15*d* (S23) and puts the injection unit 800 into the stretched state by sliding the slider 50 rearward (S24: the state in FIG. 31). Then, the user injects the chemical solution C corresponding to the amount of movement "L−P" of the gasket 20 to the injection subject or the like by pushing down the button 40 to the greatest extent possible (S25).

Figure 32:
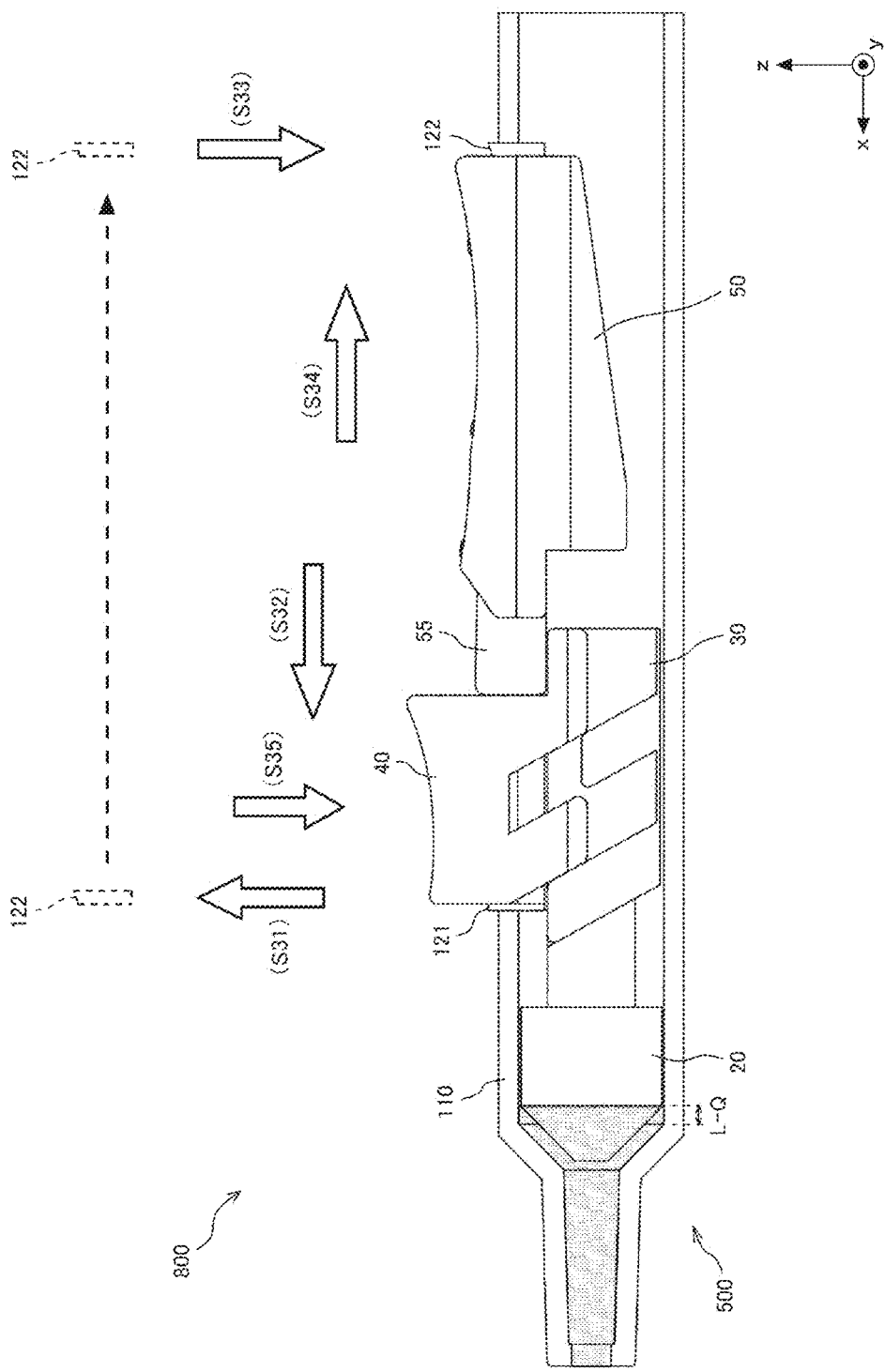
FIG. 32 is a drawing illustrating steps for administering the third largest amount of chemical solution from the injection unit in FIG. 25.

FIG. 32 corresponds to a case in which the third largest amount of chemical solution C, that is, a third amount of chemical solution C is administered from the injection unit 800. In this case, first, the user demounts the second adjustment member 122 mounted adjacent to the front wall 15*c* (S31) and removes air (S32). At this time, the gasket 20 moves forward from the position in FIG. 30 by the width Q. Then, the user mounts the second adjustment member 122 adjacent to the rear wall 15*d* (S23) and puts the injection unit 800 into the stretched state by sliding the slider 50 rearward (S34: the state in FIG. 32). Then, the user injects the chemical solution C corresponding to the amount of movement "L−Q" of the gasket 20 to the injection subject or the like by pushing down the button 40 to the greatest extent possible (S35).

Figure 33:
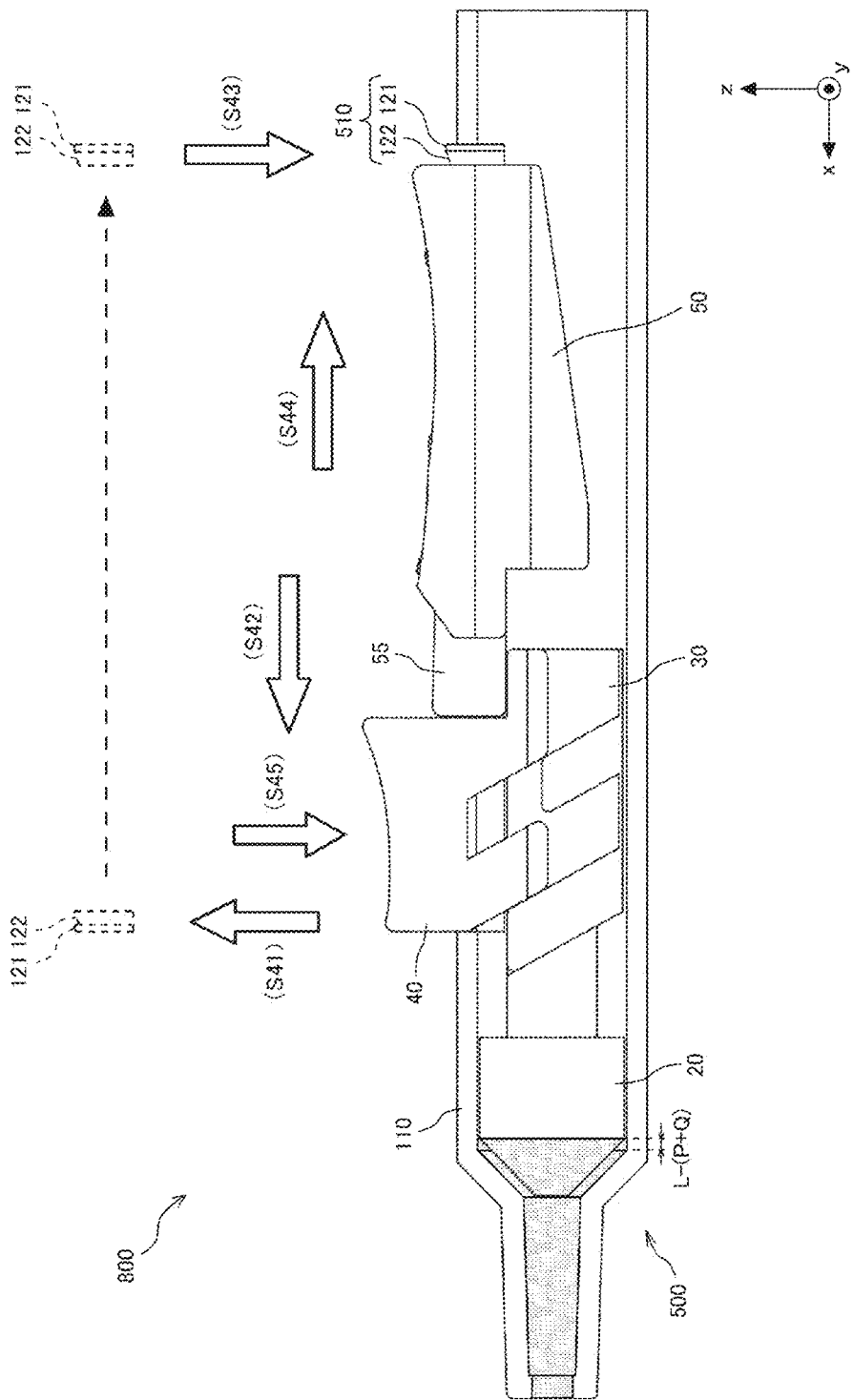
FIG. 33 is a drawing illustrating steps for administering the smallest amount of chemical solution from the injection unit in FIG. 25.

FIG. 33 corresponds to a case in which the smallest amount of chemical solution C is administered from the injection unit 800. In this case, first, the user demounts the first adjustment member 121 and second adjustment member 122 mounted adjacent to the front wall 15*c* (S41) and removes air (S42). At this time, the gasket 20 moves forward from the position in FIG. 30 by the width "P+Q". Then, the user mounts the first adjustment member 121 and second adjustment member 122 adjacent to the rear wall 15*d* (S43) and puts the injection unit 800 into the stretched state by sliding the slider 50 rearward (S44: the state in FIG. 33). Then, the user injects the chemical solution C corresponding to the amount of movement "L−(P+Q)" of the gasket 20 to the injection subject or the like by pushing down the button 40 to the greatest extent possible (S45).

For example, it is assumed that a dose of 50 μL corresponds to the amount of movement L of the gasket 20, a dose of 10 μL corresponds to the movement of the gasket 20 of 0.3 mm, the width P is 0.3 mm, and the width Q is 0.6 mm. Thus, in the case of FIG. 30, 50 μL of chemical solution C is administered; in the case of FIG. 31, 40 μL of chemical solution C is administered; in the case of FIG. 32, 30 μL of chemical solution C is administered; and in the case of FIG. 33, 20 μL of chemical solution C is administered. The largest amount, the second amount, the third amount, and the smallest amount can be changed arbitrarily by adjusting the amount of movement L corresponding to the stroke H or the width P and width Q, and/or in accordance with the size of the syringe 110 to be employed, or the like.

While the example in which the injection unit 800 includes the injection device 500 having a configuration similar to that of the injection device 100 has been described above, this example is not limiting. The injection device 500 may have a configuration similar to that of the injection device 100A, 200, 300, or 400. That is, the configuration of the third embodiment can be applied to the configuration of any of the first and second embodiments by adjusting the length of the opening 15 on the basis of the sum of the widths of the spacers 120 of the adjustment unit 510.

As with the second adjustment member 122, the first adjustment member 121 may be formed such that the width of the frame member 121*u* and the width of the spacer 121*w* are similar. Thus, when disposing the first adjustment member 121 and second adjustment member 122 in a stacked manner (FIGS. 25, 29, 30, 33), any of these members may be disposed in a more front or more rear position than the position of the other member. While the spacers 120 having a shape in which they are sandwiched between the side walls 15*b* of the opening 15, that is, a shape in which they can be fitted between the side walls 15*b* are illustrated in the drawings, this shape is not limiting. The spacers 120 may take various shapes to the extent that they can block forward movement of the button 40 in the opening 15.

As described above, the injection unit 800 includes the injection device 500 and the adjustment unit 510 including the first adjustment member 121 and second adjustment member 122. The first adjustment member 121 and second adjustment member 122 include the spacers 120 having the predetermined widths and disposed between the side walls 15*b* of the opening 15. The width P of the spacer 121*w* of the first adjustment member 121 and the width Q of the spacer 122*w* of the second adjustment member 122 are set to different lengths. Thus, the user is able to adjust the dose of the chemical solution C in four stages and thus to, for example, adjust the dose for each injection subject or adjust the dose in accordance with the physical condition, vital signs, or the like of the injection subject.

The adjustment unit 510 may consist of one adjustment member. The injection unit 800 thus configured allows the user to adjust the dose of the chemical solution C in two stages. The adjustment unit 510 may include three or more adjustment members including spacers 120 having different widths. The injection unit 800 thus configured allows the user to adjust the dose of the chemical solution C in 2*n* stages (n is the number of adjustment members).

The above embodiments are specific examples of a side push down-type injection device and injection unit, and the technical scope of the present invention is not limited to these aspects. For example, in the injection devices 100, 100A, 400, and 500 (hereafter, the reference signs are omitted) according to the embodiments, the tip-side shape of the syringes 10 and 110 is not limited to the examples in the drawings and can be changed as necessary. It is preferable to adjust the shape of the front end portion 21 of the gasket 20 in accordance with the tip-side shape of the syringe 10 or 110. The shape or the like of the lid portion 13 is not limited to the examples in the drawings and can be changed as necessary. Note that the injection device may has a configuration without the lid portion 13. The syringes 10 and 110 according to the embodiments need not have the steps 15*s* on the opening 15, or need not be formed such that the width $W_3$ near the rear wall 15*d* of the opening 15 becomes relatively narrow. That is, with respect to the syringes 10 and 110, the width of the opening 15 may be uniform over the entire area along the tip direction, or the steps 15*s* may simply be disposed, or only the width $W_3$ near the rear wall 15*d* may differ from the width of the other portions. For example, when the width near the front wall 15*c* of the opening 15 and the width near the rear wall 15*d* thereof differ from each other, the adjustment unit 510 may include an adjustment member to be mounted adjacent to the front wall 15*c* and an adjustment member to be mounted adjacent to the rear wall 15*d*.

While the examples in which the pair of leg portions 42 of the buttons 40, 40B, and 40C include the first leg portions 42*a* and second leg portions 42*b* have been described above, these examples are not limiting. That is, the leg portions 42 may consist of only the first leg portions 42*a* or may consist of only the second leg portions 42*b*. If the leg portions 42 consist of only the first leg portions 42*a*, the engaging portions 34 of the conversion portion 30 may consist of only the first engaging portion 34*a*. If the leg portions 42 consist of only the second leg portions 42*b*, the engaging portions 34 of the conversion portion 30 may consist of only the second engaging portion 34*b*. However, the leg portions 42 preferably include the first leg portions 42*a* and second leg portions 42*b* in terms of the placement stability of the button 40, the stability thereof during push-down, or the like.

While the buttons 40, 40B, and 40C including the first leg portions 42*a* and second leg portions 42*b* having the depressions 4*k* have been described in the first to third embodiments (except for the modification A), these buttons are not limiting. Only the first leg portions 42*a* of the buttons 40, 40B, and 40C may have the depressions 4*k*, or the buttons 40, 40B, and 40C may consist of leg portions having no depression 4*k*. Similarly, the leg portions 42 according to the modification A may have inwardly recessed depressions 4*k* in tip direction-side positions thereof adjacent to the side walls 15*b* of the opening 15.

The shape of the fitting portions 4*b* of the leg portions 42 of the buttons 40 and 40A to 40C according to the embodiments is not limited to the examples in the drawings. The opposed surfaces 4*r* of the fitting portions 4*b* need not be along the inner wall 12*r* of the body 12, or the fitting portions 4*b* may be formed without the protruding portions 4*m*. The buttons 40, 40B, and 40C according to the first to third embodiments may be formed without the come-out prevention portions 43. The shape of the face wall 41*a* of the buttons 40 and 40A to 40C is not limited to the examples in the drawings and can be changed arbitrarily. The surface of the face wall 41*a* may be subjected to various types of processing for increasing friction. In the conversion units 30 and 30A according to the embodiments, the engaging portions 34 only have to include one of the first engaging portion 34*a* and second engaging portion 34*b*. However, the engaging portions 34 preferably include the first engaging portion 34*a* and second engaging portion 34*b* in terms of the placement stability of the button 40, the stability thereof during push-own, or the like. While the slider 50 according to the first embodiment may be formed without the safety protrusion 55, it preferably includes the safety protrusion 55 in terms of the prevention of misoperation, or the like. While the examples in which the chemical solution C is injected into a human or animal have been described above, the injection devices may be used for applications other than such an application. For example, the injection devices may be used to inject a liquid into a food material such as pieces of meat, cells, or the like.

3s rear slope, 3t front auxiliary slope, 4a base portion, 4b, 4j fitting portion, 4f flat surface, 4h flat portion, 4k depression, 4m, 54, 64, 164, 174 protruding portions, 4r opposed surface, 4s front slope, 4t rear auxiliary slope, 10, 110 syringe, 11 tip portion, 11a ejection hole, 12 body, 12a chemical solution storage portion, 12b mechanism incorporation portion, 12c auxiliary portion, 12m peripheral wall, 12n tip portion, 12r inner wall, 13 lid portion, 15 opening, 15b side wall, 15c front wall, 15d rear wall, 15s step, 20 gasket, 21 front end portion, 30, 30A conversion portion, 31 fitting portion, 32 neck portion, 33 core portion, 34 engaging portion, 34a first engaging portion, 34b second engaging portion, 40, 40A, 40B, 40C button, 41 button body, 41a face wall, 41b side wall, 41c front end surface, 41d rear end surface, 42 leg portion, 42a first leg portion, 42b second leg portion, 43 come-out prevention portion, 45 pinching groove, 45u bottom, 50 slider, 350 slider, 51 operation portion, 51a operation surface, 51c push end surface, 51d rear end surface, 52 pinching portion, 52b bottom, 53 auxiliary portion, 53c auxiliary end surface, 55, 76, 175 safety protrusion, 55c, 65c, 75c, 76c front end surface, 60d rear end surface, 161 first operation portion, 162 first sandwiched portion, 63, 163 first auxiliary portion, 63t auxiliary protrusion, 65, 65h communication hole, 70c contact end surface, 171 second body, 172 second sandwiched portion, 173 second auxiliary portion, 75a guide groove, 75b fixing groove, 75m base portion, 75n tip portion, 85 fitting groove, 85a protruding portion, 100, 100A, 400, 500 injection device, 120, 121w, 122w spacer, 121 first adjustment member, 121u, 122u frame member, 122 second adjustment member, 160 first slider, 160A first body, 165 limitation protrusion, 170 second slider, 170A second body, 510 adjustment unit, 800 injection unit, C chemical solution, H stroke, L the amount of movement, $R_1$ region, $R_2$ region, V dose, θ set angle.

The invention claimed is:

1. An injection device comprising:
   a syringe including a tubular body, the body having, in a peripheral wall, an opening having a rectangular shape in a plan view, the opening extending from an outer surface of the peripheral wall to an inner surface of the peripheral wall;
   a conversion portion connected to a rear end portion of a gasket disposed on a tip side of the body, the conversion portion being contained in the body;
   a button disposed on the conversion portion, the button being supported by the conversion portion with side portions of the button sandwiched between both side walls of the opening; and
   a slider disposed in the opening in the peripheral wall of the body and interfacing with the outer surface of the peripheral wall, and configured to move the conversion portion and the button in a tip direction that is a direction in which the gasket moves toward a tip of the body,
   wherein the button has a cross-sectional U-shape on a plane perpendicular to the tip direction and includes a pair of leg portions disposed so as to straddle the conversion portion and having front slopes inclined with respect to the tip direction by a set angle,
   wherein the conversion portion includes a pair of engaging portions formed so as to correspond to the pair of leg portions and having rear slopes that slidingly contact the front slopes and is configured to move in the tip direction in accordance with an operation of pushing down the button toward inside of the body,
   wherein the slider includes a safety protrusion disposed on a side near the button, and
   wherein the safety protrusion is formed such that a tip surface thereof is flush with the rear end surface of the button in a state in which the button is disposed in a frontmost position in the opening and the slider is disposed in a rearmost position in the opening-;
   wherein the slider includes:
      a first slider disposed on a side near the button; and
      a second slider disposed on a side near a rear wall of the opening, wherein said first slider and said second slider are movable independently from one another;
   wherein the button has a pinching groove formed along the tip direction from a rear end surface of the button,
   wherein the first slider includes:
      a first body having a communication hole extending from a push end surface being a front end surface to a rear end surface; and
      a limitation protrusion extending in the tip direction from the first body and formed so as to be insertable into the pinching groove,
   wherein the second slider includes: an operation portion disposed outside the body and formed so as to have a wider width than a width of the opening; and,
   wherein the safety protrusion is formed so as to be insertable into the communication hole and the pinching groove, and
   wherein a tip portion of the safety protrusion is disposed on the limitation protrusion with the second slider contacting the rear end surface of the first slider.

2. An injection unit comprising:
   the injection device of claim 1; and
   one or more adjustment members configured to adjust the frontmost position of the button in the opening, wherein
   the one or more adjustment members include a spacer having a preset width and disposed between the side walls of the opening.

* * * * *